US008008256B2

(12) United States Patent
Markland, Jr. et al.

(10) Patent No.: US 8,008,256 B2
(45) Date of Patent: Aug. 30, 2011

(54) COMBINATION THERAPY FOR TREATMENT OF CANCER

(75) Inventors: Francis S Markland, Jr., Manhattan Beach, CA (US); Steven Swenson, Arcadia, CA (US); Jacek Pinski, La Canada, CA (US)

(73) Assignee: University of Southern California, Los Angeles, CA (US)

( * ) Notice: Subject to any disclaimer, the term of this patent is extended or adjusted under 35 U.S.C. 154(b) by 786 days.

(21) Appl. No.: 11/742,389

(22) Filed: Apr. 30, 2007

(65) Prior Publication Data

US 2008/0064634 A1 Mar. 13, 2008

Related U.S. Application Data

(60) Provisional application No. 60/797,030, filed on May 1, 2006.

(51) Int. Cl.
*A61K 38/00* (2006.01)
*A61K 51/00* (2006.01)
*A61P 13/06* (2006.01)
*A61P 21/02* (2006.01)
*A61M 36/14* (2006.01)

(52) U.S. Cl. .................. 514/12; 424/1.11; 424/1.65
(58) Field of Classification Search .................. None
See application file for complete search history.

(56) References Cited

U.S. PATENT DOCUMENTS

| | | | |
|---|---|---|---|
| 4,610,879 | A | 9/1986 | Markland et al. |
| 5,066,592 | A | 11/1991 | Huang et al. |
| 5,227,400 | A | 7/1993 | Holton et al. |
| 5,248,796 | A | 9/1993 | Chen et al. |
| 5,250,683 | A | 10/1993 | Holton et al. |
| 5,254,580 | A | 10/1993 | Chen et al. |
| 5,272,171 | A | 12/1993 | Ueda et al. |
| 5,278,324 | A | 1/1994 | Kingston et al. |
| 5,658,785 | A | 8/1997 | Johnson |
| 5,814,609 | A | 9/1998 | Markland et al. |
| 6,040,174 | A | 3/2000 | Imler et al. |
| 6,147,055 | A | 11/2000 | Hobart et al. |
| 6,294,374 | B1 | 9/2001 | Sinha et al. |
| 6,365,749 | B1 | 4/2002 | Kim et al. |
| 6,380,394 | B1 | 4/2002 | Nicolaou et al. |
| 6,380,395 | B1 | 4/2002 | Vite et al. |
| 6,387,927 | B1 | 5/2002 | Altmann et al. |
| 6,399,638 | B1 | 6/2002 | Vite et al. |
| 6,440,944 | B2 | 8/2002 | Bruder et al. |
| 6,441,186 | B1 | 8/2002 | Nicolaou et al. |
| 6,489,314 | B1 | 12/2002 | Ashley et al. |
| 6,498,257 | B1 | 12/2002 | Vite et al. |
| 6,518,421 | B1 | 2/2003 | Li et al. |
| 6,531,497 | B1 | 3/2003 | Nicolaou et al. |
| 6,537,988 | B2 | 3/2003 | Lee |
| 6,583,290 | B1 | 6/2003 | Julien et al. |
| 6,589,968 | B2 | 7/2003 | Arslanian et al. |
| 6,593,115 | B2 | 7/2003 | Vite et al. |
| 6,596,875 | B2 | 7/2003 | White et al. |
| 6,605,599 | B1 | 8/2003 | Vite et al. |
| 6,605,726 | B1 | 8/2003 | Mulzer et al. |
| 6,610,736 | B1 | 8/2003 | Klar et al. |
| 6,624,310 | B1 | 9/2003 | Hoefle et al. |
| 6,638,742 | B1 | 10/2003 | Hoffman |
| 6,660,758 | B1 | 12/2003 | Nicolaou et al. |
| 6,670,384 | B2 | 12/2003 | Bandyopadhyay et al. |
| 6,686,380 | B2 | 2/2004 | Lee |
| 6,689,802 | B2 | 2/2004 | DiMarco et al. |
| 6,710,030 | B1 | 3/2004 | Markland et al. |
| 6,719,540 | B2 | 4/2004 | Regueiro-Ren et al. |
| 6,727,276 | B2 | 4/2004 | Lee |
| 6,730,803 | B2 | 5/2004 | Iwasaki et al. |
| 6,780,620 | B1 | 8/2004 | Li et al. |
| 6,800,653 | B2 | 10/2004 | Regueiro-Ren et al. |
| 6,831,090 | B2 | 12/2004 | Vite et al. |
| 6,858,411 | B1 | 2/2005 | Julien et al. |
| 6,867,333 | B2 | 3/2005 | Wessjohann et al. |
| 6,878,699 | B1 | 4/2005 | Hemscheidt et al. |
| 6,893,859 | B2 | 5/2005 | Ashley et al. |
| 6,900,331 | B2 | 5/2005 | Taylor et al. |
| 6,906,188 | B2 | 6/2005 | White et al. |
| 6,921,650 | B1 | 7/2005 | Julien et al. |
| 6,930,102 | B2 | 8/2005 | Klar et al. |
| 6,930,187 | B2 | 8/2005 | Favreau et al. |
| 6,958,401 | B2 | 10/2005 | White et al. |
| 6,982,276 | B2 | 1/2006 | DiMarco et al. |
| 6,982,280 | B1 | 1/2006 | Hoefle et al. |
| 6,998,256 | B2 | 2/2006 | Arslanian |
| 7,008,936 | B2 | 3/2006 | Voi et al. |
| 7,220,724 | B2 | 5/2007 | Markland et al. |

(Continued)

FOREIGN PATENT DOCUMENTS

WO WO-00/18421 4/2000

OTHER PUBLICATIONS

Skolnick and Fetrow. From genes to protein structure and function: novel applications of computational approaches in the genomic era. Trends in Biotechnology, 2000. vol. 18, pp. 34-39.*

Burgess, Shaheen, Ravera, Jaye, Donohue, and Winkles. Possible dissociation of the heparin binding and mitogenic activities of heparin binding (acidic fibroblast) growth factor 1 from its receptor binding activities by site directed mutagenesis of a single lysine residue. Journal of Cell Biology, 1990. vol. 111, pp. 2129-2138.*

Lazar, Watanabe, Dalton and Sporn. Transforming growth factor alpha: mutation of aspartic acid 47 and leucine 48 results in different biological activities. Molecular and Cellular Biology, 1988. vol. 8, pp. 1247-1252.*

Kim, Landen, Lin, Mangala, Lu, Nick, Stone, Merritt, Armaiz-Pena, Jennings, Coleman, Tice, and Sood. Combined anti-angiogenic therapy against VEGF and integrin alpha v beta 3 in an orthotopic model of ovarian cancer. Cancer Biology and Therapy, 2009. vol. 8, pp. 2261-2270.*

(Continued)

*Primary Examiner* — Anne M. Gussow
(74) *Attorney, Agent, or Firm* — Foley & Lardner LLP

(57) ABSTRACT

The invention relates to compositions and methods for treating diseases. In particular aspects, the invention relates to administering a combination of a disintegrin with a microtubule stabilizing agent useful for treatment of cancer.

59 Claims, 4 Drawing Sheets

U.S. PATENT DOCUMENTS

| | | | |
|---|---|---|---|
| 2002/0042109 A1 | 4/2002 | Vite et al. |
| 2002/0045609 A1 | 4/2002 | Ashley et al. |
| 2002/0062030 A1 | 5/2002 | White et al. |
| 2002/0094991 A1 | 7/2002 | Gallaher |
| 2002/0143038 A1 | 10/2002 | Bandyopadhyay et al. |
| 2002/0156110 A1 | 10/2002 | Arslanian et al. |
| 2002/0165257 A1 | 11/2002 | Lee |
| 2002/0165258 A1 | 11/2002 | Lee |
| 2002/0169190 A1 | 11/2002 | Bandyopadhyay et al. |
| 2002/0188014 A1 | 12/2002 | DiMarco et al. |
| 2002/0193361 A1 | 12/2002 | Ashley et al. |
| 2003/0004338 A1 | 1/2003 | Li et al. |
| 2003/0023082 A1 | 1/2003 | Ashley et al. |
| 2003/0045711 A1 | 3/2003 | Ashley et al. |
| 2003/0060623 A1 | 3/2003 | Vite et al. |
| 2003/0073677 A1 | 4/2003 | Lee |
| 2003/0087888 A1 | 5/2003 | Regueiro-Ren et al. |
| 2003/0144523 A1 | 7/2003 | Klar et al. |
| 2003/0144533 A1 | 7/2003 | Iwasaki et al. |
| 2003/0149281 A1 | 8/2003 | Westermann et al. |
| 2003/0176473 A1 | 9/2003 | Taylor et al. |
| 2003/0176710 A1 | 9/2003 | Klar et al. |
| 2003/0186884 A1 | 10/2003 | Markland et al. |
| 2003/0186965 A1 | 10/2003 | Vite et al. |
| 2003/0187039 A1 | 10/2003 | Favreau et al. |
| 2003/0187273 A1 | 10/2003 | White et al. |
| 2003/0191089 A1 | 10/2003 | Regueiro-Ren et al. |
| 2003/0203938 A1 | 10/2003 | Nicolaou et al. |
| 2003/0219877 A1 | 11/2003 | Tang et al. |
| 2003/0220295 A1 | 11/2003 | Vite et al. |
| 2003/0220503 A1 | 11/2003 | Mulzer et al. |
| 2004/0014978 A1 | 1/2004 | Klar et al. |
| 2004/0022869 A1 | 2/2004 | Chen et al. |
| 2004/0023345 A1 | 2/2004 | Vite et al. |
| 2004/0024032 A1 | 2/2004 | Voi et al. |
| 2004/0030147 A1 | 2/2004 | White et al. |
| 2004/0038324 A1 | 2/2004 | Atadja et al. |
| 2004/0039026 A1 | 2/2004 | Nicoloou et al. |
| 2004/0049051 A1 | 3/2004 | Hoefle et al. |
| 2004/0052785 A1 | 3/2004 | Goodman et al. |
| 2004/0053978 A1 | 3/2004 | Lee et al. |
| 2004/0058969 A1 | 3/2004 | Buchmann et al. |
| 2004/0072870 A1 | 4/2004 | Nicolaou et al. |
| 2004/0072882 A1 | 4/2004 | Johnson et al. |
| 2004/0082651 A1 | 4/2004 | Wessjohann et al. |
| 2004/0092478 A1 | 5/2004 | Rothermel et al. |
| 2004/0127432 A1 | 7/2004 | Nicolaou et al. |
| 2004/0132146 A1 | 7/2004 | Benigni et al. |
| 2004/0132754 A1 | 7/2004 | Brandt et al. |
| 2004/0157897 A1 | 8/2004 | DiMarco et al. |
| 2004/0176429 A1 | 9/2004 | Li et al. |
| 2004/0214871 A1 | 10/2004 | Lee |
| 2004/0253697 A1 | 12/2004 | Julien et al. |
| 2004/0259922 A1 | 12/2004 | Hoefle et al. |
| 2005/0038086 A1 | 2/2005 | Ashley et al. |
| 2005/0042275 A1 | 2/2005 | Sonntag et al. |
| 2005/0113429 A1 | 5/2005 | Klar et al. |
| 2005/0148657 A1 | 7/2005 | Zygmunt et al. |
| 2005/0159461 A1 | 7/2005 | Lee |
| 2005/0187270 A1 | 8/2005 | Klar et al. |
| 2005/0192440 A1 | 9/2005 | White et al. |
| 2005/0267306 A1 | 12/2005 | Westermann et al. |
| 2005/0282873 A1 | 12/2005 | Rothermel |
| 2006/0013836 A1 | 1/2006 | Bandyopadhyay et al. |
| 2006/0014796 A1 | 1/2006 | Denni-Dischert et al. |
| 2006/0040990 A1 | 2/2006 | Klar et al. |
| 2006/0046997 A1 | 3/2006 | Klar et al. |
| 2006/0063815 A1 | 3/2006 | DiMarco et al. |
| 2006/0246541 A1 | 11/2006 | Minea et al. |
| 2007/0123458 A1 | 5/2007 | Markland et al. |

OTHER PUBLICATIONS

Ahmed, Mills, Ibrahim, Temple, Blenkiron, Vias, Massie, Iyer, MC Geoch, Crawford, Nicke, Downward, Swanton, Bell, Earl, Laskey, Caldas, and Brenton. The extracellular matrix protein TGFB1 induces microtubule stabilization and sensitizes ovarian cancers to paclitaxel. Cancer Cell, 2007. vol. 12, pp. 514-527.*

Mattern et al., "Giloma cell integrin expression and their interactions with integrin antagonists", Cancer Therapy, vol. 3, pp. 325-340, 2005.

European Search Report dated Dec. 30, 2009 for EP Application No. 06849695.9.

International Search Report dated Jun. 2, 2008 for PCT Application No. PCT/US06/04413.

Interview Summary dated Aug. 11, 2009 for U.S. Appl. No. 11/351,311.

McLane et al., Proceedings of the Society for Experimental Biology and Medicine, Proc. Soc. Exp. Biol. Med., 219(2):109-119 (1998).

Minea et al., Development of a novel recombinant disintegrin, contortrostatin, as an effective anti-tumor and anti-angiogenic agent. Pathophysical Haemost Thromb (2005) 34(4-5): 177-183.

Notice of Allowance dated Feb. 4, 2010 for U.S. Appl. No. 11/351,311.

Notice of Allowance dated Aug. 24, 2009 for U.S. Appl. No. 11/351,311.

Office Action dated Feb. 19, 2008 for U.S. Appl. No. 11/351,311.

Office Action dated May 8, 2009 for U.S. Appl. No. 11/351,311.

Office Action dated Sep. 4, 2008 for U.S. Appl. No. 11/351,311.

Swenson et al., Chimeric derivative of fibrolase, a fibrinolytic enzyme from southern copperhead venom, possesses inhibitory activity on platelet aggregation, Arch. Biochem. Biophys., (2000), 384(2):227-237.

Swenson et al., Intravenous Liposomal Delivery of the Snake Venom Disintegrin Contortrostatin Limits Breast Cancer Progression, Mol. Cancer Ther., 3(4):499-511 (2004).

Zhou et al., Contortrostatin, a Dimeric Disintegrin from *Agkistrodon contortrix contortrix*, Inhibits Breast Cancer Progression, Breast Cancer Research and Treatment, 61(3):249-260 (2000).

Chao B. H. et al., *Agkistrodon piscivorus piscivorus* platelet aggregation inhibitor: A potent inhibitor of platelet activation, Proc. Natl. Acad. Sci. USA 86:8050-8054 (1989).

Choudhary et al., Two New Rearranged Taxoids from *Taxus wallichiana* Zucc, Chem. Pharm. Bull. 50(11): 1488-1490 (2002).

Connolly et al., Antithrombotic Effect of the Factor Xa Inhibitor Tick Anticoagulant Peptide (TAP) in a Baboon Model of Acute Arterial Thrombosis, Circulation, vol. 82, No. 4, (Suppl. III), pp. 660 (1990).

Gan et al., A Potent Platelet Aggregation Inhibitor From the Venom of the Viper, *Echis carinatus*, J. Biol. Chem. 263(36):19827-19832 (1988).

Giannakakou et al., A common pharmacophore for epothilone and taxanes: Molecular basis for drug resistance conferred by tubulin mutations in human cancer cells, PNAS 97(6):2904-2909 (2000).

Golubkov et al., Anti-angiogenic activity of contortrostatin, a disintegrin from *Agkistrodon contortrix contortrix* snake venom, Angiogenesis 6:213-224 (2003).

Holahan et al., Prevention of Reocculsion following Tissue Type Plasminogen Activator-Induced Thrombolysis by the RGD-Containing Peptide, Echistatin, in a Canine Model of Coronary Thrombosis, Pharmacology 42:340-348 (1991).

Holton et al., First Total Synthesis of Taxol. 1. Functionalization of the B Ring, J. Am. Chem. Soc. 116:1597-1598 (1994).

Huang et al., A Low Molecular Weight Peptide Inhibiting Fibrinogen Interaction With Platelet Receptors Expressed on Glycoprotein IIb-IIIa Complex, J. Biol. Chem. 262(33):16157-16163 (1987).

Jennewein et al., Taxol biosynthesis: Taxine 13 α-hydroxylase is a cytochrome P450-dependent monooxygenase, PNAS 98(24):13595-13600 (2001).

Kang et al., A Novel Disintegrin Salmosin Inhibits Tumor Angiogenesis, Cancer Research 59:3754-60 (1999).

Kowalski et al., The Microtubule-Stabilizing Agent Discodermolide Competitively Inhibits the Binding of Paclitaxel (Taxol) to Tubulin Polymers, Enhances Tubulin Nucleation Reactions More Potently than Paclitaxel, and Inhibits the Growth of Paclitaxel-Resistant Cells, Mol. Pharm. 52:613-622 (1997).

Levy et al., Gemcitabine plus docetaxel: a new treatment option for anthracycline pretreated metastatic breast cancer patients?, Cancer Treat. Rev., vol. 31 (Suppl. 4), pp. S17-22 (2005).

Madiraju et al., Tubulin Assembly, Taxoid Site Binding, and Cellular Effects of the Microtubule-Stabilizing Agent Dictyostatin, Biochem. 44:15053-15063 (2005).

Mani et al., Phase I Clinical and Pharmacokinetic Study of BMS-247550, a Novel Derivative of Epothilone B, in Solid Tumors, Clin. Cancer Res. 10:1289-1298 (2004).

Markland et al, Snake Venom Disintegrin: An Effective Inhibitor of Breast Cancer Growth and Dissemination, Chapter 18 in Natural and Selected Synthetic Toxins, Biological Implications, Tu, A.T. et al. editors, ACS Symposium Series, 745:262-282 (2000).

Markland et al., A Novel Snake Venom Disintegrin That Inhibits Human Ovarian Cancer Dissemination and Angiogenesis in an Orthotopic Nude Mouse Model, Haemostasis 31(3-6): 183-191 (2001).

McLane et al., Viper Venom Disintegrins and Related Molecules (44322), Proc Soc. Exp. Biol. Med. 219(2):109-119 (1998).

Mooberry et al., Microtubule-stabilizing agents based on designed laulimalide analogues, PNAS 101(23) 8803-8808 (2004).

Ono et al., Absorption, Distribution, and Excretion of DJ-927, A Novel Orally Effective Taxane, in Mice, Dogs, and Monkeys, Biol. Pharm. Bull. 27(3): 345-351 (2004).

Pinski et al., A novel therapy for prostate cancer based on the disintegrin contortrostatin, Proc. Am. Soc. Clin. Oncol. 22, (Abstract—1 pg.) (2003).

Rose et al., Therapeutic Synergy of Oral Taxane BMS-275183 and Cetuximab versus Human Tumor Xenografts, Clin. Cancer Res. 10:7413-7417 (2004).

Sampath et al., MAC-321, a novel taxane with greater efficacy than paclitaxel and docetaxel in vitro and in vivo, Mol. Cancer Ther. 2(9):873-74 (2003).

Savage et al., Binding of the Snake Venom-derived Proteins Applaggin and Echistatin to the Arginine-Glycine-Aspartic Acid Recognition Site(s) on Platelet Glycoprotein IIb-IIIa Complex Inhibits Receptor Function, J. Biol. Chem. 265(20):11766-11772 (1990).

Scarborough et al., A GPIIb-IIIa-Specific Integrin Antagonist From the Venom of *Sistrurus M. barbouri*, J. Biol. Chem. 266(15):9359-9362 (1991).

Schmitmeier et al., Anti-invasive Effect of Contortrostatin, a Snake Venom Disintegrin, and TNF-α on Malignant Glioma Cells, Anticancer Res. 20:4227-4233 (2000).

Shebuski et al., Acceleration of Recombinant Tissue-Type Plasminogen Activator-Induced Thrombolysis and Prevention of Reocclusion by the Combination of Heparin and the Arg-Gly-Asp-Containing Peptide Bitistatin in a Canine Model of Coronary Thrombosis, Circulation 82(1):169-177 (1990).

Shen et al., New Bicyclic Taxane Diterpenoids from *Taxus sumatrana*, Chem. Pharm. Bull. 53(7):808-810 (2005).

Trikha et al., A Novel Platelet aggregation inhibitor from southern copperhead snake venom, Fibrinolysis, vol. 4 (Suppl. 1):105 (1990).

Trikha et al., Characterization of a Novel Platelet Aggregation Inhibitor (ContortrostatIn) From the Southern Copperhead Snake Venom, Blood, vol. 76, No. 10 (Suppl. 1):479a (1990).

Trikha et al., Contortrostatin, a Snake Venom Disintegrin, Ingihibts $\beta_1$ Integrin-mediated Human Metastatic Melanoma Cell Adhesion and Blocks Experimental Metastasis, Cancer Res. 54: 4993-4998 (1994).

Trikha et al., Purification and Characterization of Platelet Aggregation Ingibitors Frome Snake Venoms, Thrombosis Res. 73(1):39-52 (1994).

Villalva-Servín et al., Part 2: Efficient strategies for the construction of variably substituted bicyclo[5.3.1]undecenones (AB-taxane right systems) and their conversion to tricyclo[9.3.1.0$^{3,8}$]pentadecoenones (ABC taxane ring systems) and bicyclo[2.2.2]octanones, Can. J. Chem. 82:227-239 (2004).

Wolff et al., Phase I Study of Docosahexaenoic Acide-Paclitaxel: A Taxane-Fatty Acid Conjugate with a Unique Pharmacology and Toxicity Profile, Clin. Cancer Res. 9:3589-3597 (2003).

Yasuda et al, Comparative Effects of Aspirin, a Synthetic Thrombin Inhibitor and a Monoclonal Antiplatelet Glycoprotein IIb/IIIa Antibody on Coronary Artery Reperfusion, Reocclusion and Bleeding With Recombinant Tissue-Type Plasminogen Activator in a Canine Preparation, JACC 16(3):714-722 (1990).

Yasuda et al., Kistrin, A Polypeptide Platelet GPIIb/IIIa Receptor Antagonist, Enhances and Sustains Coronary Arterial Thrombolysis With Recombinant Tissue-Type Plasminogen Activator in a Canine Preparation, Circulation 83(3):1038-1047 (1991).

Yeh et al, Accutin, a New Disintegrin, Inhibits Angiogenesis in Vitro and in Vivo by Acting as Integrin $\alpha_v\beta_3$ Antagonist and Inducing Apoptosis, Blood, vol. 92, No. 9, pp. 3268-3276 (1998).

Zhou et al, Contortrostatin, A Snake Venom Protein, Which Is an Inhibitor of Breast Cancer Progression, Molecular Biology of the Cell, No. 7, Suppl., p. 425A (1996).

Zhou et al., Contortrostatin, a dimeric disintegrin from *Agkistrodon contortrix contortrix*, inhibits angiogenesis, Angiogenesis 3(3):259-269 (1999).

Zhou et al., Contortrostatin, a dimeric disintegrin from *Agkistrodon contortrix contortrix*, inhibits breast cancer progression, Breast Cancer Res. Treat. 61:249-260 (2000).

Zhou et al., Contortrostatin, a Homodimeric Disintegrin, Binds to Integrin $\alpha_v\beta_5$ Biochem. Biophys. Res. Commun. 267:350-355 (2000).

Zhou et al., Molecular Cloning and Functional Expression of Contortrostatin, A Homodimeric Disintegrin From Southern Copperhead Snake Venom, Biochem. Biophys. 375(2): 278-288 (2000).

Beekman et al, Phase II evaluations of Cilengitide in asymptomatic patients with androgen-independent prostate cancer: scientific rationale and study design, Clinical Genitourinary Cancer, Mar. 2006, 4(4):299-302.

Bergstralh et al, Microtubule stabilizing agents: Their molecular signaling consequences and the potential for enhancement by drug combination, Cancer Treatment Reviews, Mar. 9, 2006, 32(3):166-179.

Inoue et al, Docetaxel enhances the therapeutic effect of the angiogenesis inhibitor TNP-470 (AGM-1470) in metastatic human transitional cell carcinoma, Clinical Cancer Research: An Official Journal of the American Associate for Cancer Research, Feb. 2003, 9(2):886-899.

Marcinkiewicz, C., Functional characteristic of snake venom disintegrins: potential therapeutic implication, Current Pharmaceutical Design, 2005, 11(7):815-827.

Miles et al, Combination versus sequential single-agent therapy in metastatic breast cancer, The Oncologist, 2002, 7(sup. 6):13-19.

Supplemental European Search Report dated Jun. 21, 2010 for EP Application No. 07776668.1.

Communication pursuant to Article 94(3) EPC in EP application 07776668.

* cited by examiner

FIGURE 2

```
Met Ile Gln Val Leu Leu Val Thr Leu Cys Leu Ala Ala Phe Pro Tyr
1               5                   10                  15
Gln Gly Ser Ser Ile Ile Leu Glu Ser Gly Asn Val Asn Asp Tyr Glu
            20                  25                  30
Val Leu Tyr Pro Gln Lys Val Thr Ala Leu Pro Lys Gly Ala Val Gln
            35                  40                  45
Pro Lys Tyr Glu Asp Thr Met Gln Tyr Glu Phe Lys Val Asn Gly Glu
        50                  55                  60
Pro Val Val Leu His Leu Glu Lys Asn Lys Gly Leu Phe Ser Lys Asp
65                  70                  75                  80
Tyr Ser Glu Thr His Tyr Ser Ser Asp Gly Arg Lys Ile Thr Thr Asn
                85                  90                  95
Pro Pro Val Glu Asp His Cys Tyr Tyr His Gly Arg Ile Gln Asn Asp
                100                 105                 110
Ala Asp Ser Thr Ala Ser Ile Ser Ala Cys Asn Gly Leu Lys Gly His
            115                 120                 125
Phe Lys Leu Gln Gly Glu Thr Tyr Leu Ile Glu Pro Leu Lys Leu Ser
        130                 135                 140
Asp Ser Glu Ala His Ala Val Tyr Lys Tyr Glu Asn Val Glu Lys Glu
145                 150                 155                 160
Asp Glu Ala Pro Lys Met Cys Gly Val Thr Gln Thr Asn Trp Glu Ser
                165                 170                 175
Asp Glu Pro Ile Lys Lys Ala Ser Gln Leu Asn Leu Thr Pro Glu Gln
            180                 185                 190
Gln Gly Phe Pro Gln Arg Tyr Ile Glu Leu Val Val Val Ala Asp His
            195                 200                 205
Arg Met Phe Thr Lys Tyr Asn Gly Asn Leu Asn Thr Ile Arg Ile Trp
        210                 215                 220
Val His Glu Leu Val Asn Thr Met Asn Val Phe Tyr Arg Pro Leu Asn
225                 230                 235                 240
Ile Arg Val Ser Leu Thr Asp Leu Glu Val Trp Ser Asp Gln Asp Leu
            245                 250                 255
Ile Asn Val Gln Pro Ala Ala Ala Asp Thr Leu Glu Ala Phe Gly Asp
            260                 265                 270
Trp Arg Glu Thr Val Leu Leu Asn Arg Ile Ser His Asp Asn Ala Gln
```

FIGURE 2 (CONTINUED)

```
            275                 280                 285
Leu Leu Thr Ala Ile Glu Leu Asp Gly Glu Thr Ile Gly Leu Ala Asn
        290                 295                 300
Arg Gly Thr Met Cys Asp Pro Lys Leu Ser Thr Gly Ile Val Gln Asp
305                 310                 315                 320
His Ser Ala Ile Asn Leu Trp Val Ala Val Thr Met Ala His Glu Met
                325                 330                 335
Gly His Asn Leu Gly Ile Ser His Asp Gly Asn Gln Cys His Cys Asp
                340                 345                 350
Ala Asn Ser Cys Ile Met Ser Glu Glu Leu Arg Glu Gln Leu Ser Phe
            355                 360                 365
Glu Phe Ser Asp Cys Ser Gln Asn Gln Tyr Gln Thr Tyr Leu Thr Asp
        370                 375                 380
His Asn Pro Gln Cys Met Leu Asn Glu Pro Leu Arg Thr Asp Ile Val
385                 390                 395                 400
Ser Thr Pro Val Ser Gly Asn Glu Leu Leu Glu Thr Gly Glu Glu Ser
                405                 410                 415
Asp Phe Asp Ala Pro Ala Asn Pro Cys Cys Asp Ala Ala Thr Cys Lys
                420                 425                 430
Leu Thr Thr Gly Ser Gln Cys Ala Asp Gly Leu Cys Cys Asp Gln Cys
            435                 440                 445
Lys Phe Met Lys Glu Gly Thr Val Cys Arg Arg Ala Arg Gly Asp Asp
        450                 455                 460
Leu Asp Asp Tyr Cys Asn Gly Ile Ser Ala Gly Cys Pro Arg Asn Pro
465                 470                 475                 480
Phe His Ala
```

FIGURE 3

```
gaattcgggg tcaatagagg aagagctcaa gttggcttga aagcaggaag agattgcctg      60
tcttccagcc aaatccagcc gccaaaatga tccaggttct cttggtgact ctatgcttag     120
cagcttttcc ttatcaaggg agctctataa tcctggaatc tgggaatgtt aatgattatg     180
aagtactgta tccacaaaaa gtcactgcat tgcccaaagg agcagttcag ccaaagtatg     240
aagacaccat gcaatatgaa tttaaagtga atggagagcc agtggtcctt cacctggaaa     300
aaaataaagg actttttca aaagattaca gcgagactca ttattcctct gatggcagaa      360
aaattacaac aaaccctccg gttgaggatc actgctatta tcatggacgc atccagaatg     420
atgctgactc aactgcaagc atcagtgcat gcaacggttt gaaaggacat ttcaagcttc     480
aaggggagac gtaccttatt gaaccottga agctttccga cagtgaagcc catgcagtct     540
acaaatatga aaacgtagaa aagaagatg  aggcccccaa aatgtgtggg gtaacccaga     600
ctaattggga atcagatgag cccatcaaaa aggcctctca gttaaatctt actcctgaac     660
aacaaggatt cccccaaaga tacattgagc ttgttgtagt tgcagatcac agaatgttca     720
cgaaatacaa cggcaatttta aatactatta gaatatgggt acatgaactt gtcaacacta     780
tgaatgtgtt ttacagacct ttgaatattc gtgtctcact gactgaccta gaagtttggt     840
cagaccaaga tttgatcaac gtgcagccag cagcggctga tactttggaa gcatttggag     900
actggagaga gacagtcttg ctgaatcgca taagtcatga taatgctcag ttactcacgg     960
ccattgagct tgatggagaa actataggat tggctaacag gggcaccatg tgcgacccga    1020
agctttctac aggaattgtt caggatcata gtgcaataaa tctttgggtt gcagttacaa    1080
tgccccatga gatgggtcat aatctgggta ttagtcacga tggaaatcag tgtcattgcg    1140
atgctaactc atgcattatg agtgaagaac taagagaaca actttccttt gagttcagcg    1200
attgtagtca gaatcaatat cagacatatc ttactgatca taacccacaa tgcatgctca    1260 atgaacccttt gagaacagat attgtttcaa ctccagtttc tggaaatgaa cttttggaga    1320
cgggagaaga aagtgacttt gacgctcctg caaatccgtg ctgcgatgct gcaacatgta    1380
aactgacaac agggtcacag tgtgcagatg gactgtgttg tgaccagtgc aaatttatga    1440 agaaggaac agtatgccgg agagcaaggg gtgatgacct ggatgattac tgcaatggca    1500
tatctgctgg ctgtccaga aatcccttcc atgcctaacc aacaatggag atggaatggt     1560
ctgcagcaac aggcagtgtg ttgatctgaa tacagcctaa taatcaacct ctggcttctc    1620
tcagatttga tcatggagat ccttcttcca gaaggtttca cttccctcaa atccaaagag    1680
acccatctgc ctgcatccta ctagtaaatc accttagct tccagatggt atccaaattc    1740
tgtaatattt cttctccata tttaatctat ttaccttttg ctgtaacaaa accttttcc    1800 tgtcacaaag ctccatgggc atgtacagct tatctgctgt caagaaaaaa aatggccatt    1860
ttaccgtttg ccagttacaa agcacattta atgcaacaag ttcttccttt tgagctgatg    1920
tattcaaagt caatgcttcc tctcccaaaa tttcatgctg gcttcccaag atgtagctgc    1980
ttccgtcaat aaacaaacta ttctcattca aaaaaaaaaa cccgaattc                2029
```

COMBINATION THERAPY FOR TREATMENT OF CANCER

CROSS-REFERENCE TO RELATED APPLICATIONS

This application claims the benefit of priority under 35 U.S.C. §119(e) to U.S. Provisional Application Ser. No. 60/797,030 filed May 1, 2006, which is incorporated by reference herein in its entirety including all figures and tables.

STATEMENT OF GOVERNMENT SUPPORT

This invention was made with government support under Contract No. W81XWH-04-1-0817 awarded by the US Army Medical Research and Material Command. The government has certain rights in the invention.

FIELD OF THE INVENTION

The invention relates to compositions and methods for treating diseases. In particular aspects, the invention relates to administering a combination of a disintegrin with a microtubule stabilizing agent useful for treatment of cancer.

SEQUENCE LISTING

The instant application contains a Sequence Listing which has been submitted via EFS-Web and is hereby incorporated by reference in its entirety, Said ASCII copy, created on Apr. 29, 2010 is named 07540512.txt, and is 24,000 bytes in size.

BACKGROUND OF THE INVENTION

The first step of metastasis involves the attachment of cancer cells to tissues around the primary site, i.e., to the extracellular matrix (ECM) via cell surface integrins and other adhesion receptors. Integrin targets of the ECM include fibronectin, fibrinogen, vitronectin, collagen and laminin. Integrins mediate cell-cell and cell-substratum interactions and are involved in bidirectional signaling that links the ECM with cytoskeletal proteins. In the second step, cancer cells secrete digestive enzymes that degrade the surrounding tissues allowing the tumor cells to invade these tissues. Eventually, the tumor cells enter the blood or lymphatic system where they repeat the adhesion and invasion steps at a distant (metastatic) site. At this remote site, tumor cells induce the formation of new blood vessels (a process called neovascularization), in and around the growing tumor. These new blood vessels supply nutrients to the metastatic tumor and allow it to grow. Treatments that block any of these steps should act to inhibit metastasis.

Integrins are heterodimers composed of alpha and beta submits that are non-covalently associated. Interactions between integrins and ECM proteins have been shown to be mediated via an Arg-Gly-Asp (RGD) sequence present in the matrix proteins. Both the alpha and beta subunits of the integrin are required for fibrinogen binding.

A well known inhibitor of the integrin-ECM interaction is a disintegrin which represents a family of proteins that include those from venom of snakes of the Crotalidae and Viperidae families have been found to inhibit glycoprotein (GP) IIb/IIIa mediated platelet aggregation. See, e.g., Huang, T. F. et al., J. Biol. Chem. 262:16157 (1987); Gan, Z. R. et al., J. Biol. Chem. 263:19827 (1988); Yasuda, T. et al., J. Am. Coll. Cardiol. 16:714 (1990); Trikha, M. et al., Fibtinolysis 4 (Suppl. 1):105 (1990); Trikha, M. et al., Blood 76 (Suppl. 1):479a (1990); Holahan, M. A. et al., Pharmacology 42:340 (1991); Shebuski, R. J. et al., Circulation 82:169 (1990); Yasuda, T. et al., Circulation 83:1038 (1991). Disintegrins are disulfide rich and, with the exception of barbourin, contain an RGD (Arg-Gly-Asp) sequence that has been implicated in the inhibition of integrin-mediated interactions (Scarborough et al., J. Biol. Chem. 266(20):9359-62 (1991)). Most disintegrins can disrupt different integrin-ECM interactions (e.g., inhibition of β1 integrins (McLane et al. 1998) and β3 integrins such as barbourin are relatively specific and disrupt only αIIbβ3 integrin function (Scarborough et al. (1991)).

The RGD sequence of disintegrins is located at the tip of a flexible loop, the integrin-binding loop, stabilized by disulfide bonds and protruding from the main body of the polypeptide chain. See, e.g., amino acid residues 457 to 469 of SEQ ID NO: 1. This exposed RGD sequence enables disintegrins to bind to integrins with high affinity. Portions of a disintegrin other than the RGD site may have biological effects on integrins. See, e.g., Connolly, T. M. et al., Circulation 82 (Suppl. III):660 (1990)).

Disintegrins that are known to disrupt integrin interactions include bitistatin, an 83 amino acid disintegrin isolated from the venom of *Bitis arietans*; echistatin, a 49 amino acid disintegrin isolated from the venom of *Echis cannatus*; kistrin, a 68 amino acid disintegrin isolated from the venom of *Calloselasma rhodostoma*; trigamin, a 72 amino acid disintegrin isolated from the venom of *Trimeresurus gramineus*, (see U.S. Pat. No. 5,066,592 by Huang et al.); applaggin, isolated from the venom of *Agkistrodon piscivorus piscivorus* (see e.g., Chao, B. H. et al., Proc. Natl. Acad. Sci. USA 86:8050 (1989); Savage, B. et al., J. Biol. Chem. 265:11766 (1990)); and contortrostatin (CN), isolated from the venom of *Agkistrodon contortix contortix* (the southern copperhead snake).

Unlike other monomeric disintegrins, CN is a homodimer with molecular mass (Mr) of 13,505 for the intact molecule and 6,750 for the reduced chains as shown by mass spectrometry (Trikha, Rote, et al., Thrombosis Research 73:39-52 (1994)). CN can be purified from snake venom, as described in Trikha, Rote, et al., Thrombosis Research 73:39-52 (1994).

CN full-length DNA precursor has been cloned and sequenced (Zhou, Hu et al. (2000)). CN is produced in the snake venom gland as a multidomain precursor of 2027 bp having a 1449 bp open reading frame encoding a precursor that includes a pro-protein domain (amino acid residues 1 to 190 of SEQ ID NO: 1), a metalloproteinase domain (residues 191 to 410 of SEQ ID NO: 1) and a disintegrin domain (residues 419 to 483 of SEQ ID NO: 1). The CN precursor is proteolytically processed, possibly autocatalytically, to generate mature CN. The CN disintegrin domain encodes 65 amino acids with a molecular weight equal to that of the mature CN subunit. CN displays the classical RGD motif in its integrin-binding loop.

The CN full-length precursor mRNA sequence can be accessed in the GenBank database using accession number: AF212305. The nucleotide sequence encoding the 65 amino acid disintegrin domain of CN represents the segment from 1339 to 1533 in the mRNA. Plasmids encoding the CN full-length gene have been described (Zhou, Hu et al. (2000)) and are available from the laboratory of Francis S. Markland at University of Southern California (Los Angeles, Calif.). Various recombinant forms of CN are disclosed in U.S. Pat. No. 6,710,030 by Markland.

CN is cysteine-rich (10 cysteines per monomer), displays no secondary structure and, like other disintegrins, has a complex folding pattern that relies on multiple disulfide bonds (four intrachain and two interchain disulfide bonds) to stabilize its tertiary structure (Zhou, Hu et al. (2000)). The compact structure of CN, achieved by its multiple disulfide bonds, renders it more resistant to proteolytic inactivation as compared to other disintegrins.

Receptors of CN that have been identified include: integrins αIIbβ3, αvβ3, αvβ5, and α5β1 (Trikha, De Clerck et al., Cancer Res. 54(18): 4993-98 (1994); Trikha, Rote et al., Thrombosis Res. 73(1): 39-52 (1994); Zhou, Nakada et al., Angiogenesis 3(3): 259-69 (1999); Zhou, Nakada et al., Biochem. Biophys. Res. Commun. 267(1): 350-55 (2000). Interactions between CN and integrins are RGD-dependent. As an anti-cancer agent, CN has effective anti-angiogenic and anti-metastatic properties (Trikha, De Clerck et al. 1994; Trikha, Rote et al. (1994); Schmitmeier et al., Anticancer Res. 20(6B): 4227-33 (2000); Zhou, Hu et al., Biochem. Biophys. 375(2): 278-88 (2000); Markland et al., Haemostasis 31(3-6): 183-91 (2001); Swenson et al., Mol. Cancer Ther. 3(4): 499-511 (2004)). CN also has the ability to directly engage tumor cells and suppress their growth in a cytostatic manner (Trikha, De Clerck et al. (1994); Trikha, Rote et al. (1994); Schmitmeier et al. (2000)). The antitumoral activity of CN is based on its high affinity interaction with integrins α5β1, αvβ3 and αvβ5 on both cancer cells and newly growing vascular endothelial cells (Trikha, De Clerck et al. (1994); Zhou, Nakada et al. (1999); Zhou, Nakada et al. (2000); Zhou, Sherwin et al., Breast Cancer Res. Treat. 61(3): 249-60 (2000)). This diverse mechanism of action provides CN with a distinct advantage over many antiangiogenic agents that only block a single angiogenic pathway and/or do not directly target tumor cells.

The taxanes represent a class of small molecule diterpenoids compounds (i.e., taxoids) that are useful for cancer therapy. Paclitaxel (Taxol®) and docetaxel (Taxotere®), are well known taxanes which are efficacious against a range of solid tumors, particularly carcinomas, melanomas, and sarcomas. (See e.g., references cited in Pamela et al., Clin Cancer Res Vol. 8, 846-855 (2002)). Paclitaxel and docetaxel bind to β tubulin and disrupt microtubule assembly/disassembly. Id. Stabilization of microtubules by taxanes causes mitotic arrest and cell death (e.g., apoptosis) reportedly independent of the p53 tumor suppressor. Id. Taxanes induce genes encoding inflammatory mediators such as tumor necrosis factor alpha, interleukins, and enzymes such as NO synthase and COX-2. Id.

Taxanes have a common "taxoid" core structure shown below.

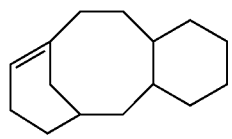

Taxoid core

Taxol® was first isolated from the bark of the Pacific yew (Taxus brevifolia Nutt.) but is presently derived mainly by semisynthesis from the advanced taxoid 10-deacetylbaccatin III, which can be obtained from bark or needles of the European yew, Taxus baccata. (See e.g., references 15-20 in Jennewein, et al., PNAS, 98(24):13595-13560 (2001); see also Holton, et al., J. Am. Chem. Soc., 116:1597-1601 (1994)).

A number of modified taxanes or taxoid analogs have been prepared which have a taxane ring bearing modified side chains. These modified taxanes or taxoid analogs inhibit cancer growth while having greater water solubility and stability than naturally occurring Taxol®. Analogs also include fatty acid conjugates. Exemplary derivatives of Taxol® are described in U.S. Pat. Nos. 6,638,742; 5,278,324; 5,272,171; 5,254,580; 5,250,683; 5,248,796; and 5,227,400; and U.S. Pub. App. No. 2005/0148657; and the references cited therein, as well as those compounds disclosed in Villalva-Servín, et al., Can. J. Chem., 82: 227-39 (2004); Shen, et al., Chem. Pharm. Bull., 53(7): 808-10 (2005); Ono, et al., Biol. Pharm. Bull., 27(3): 345-51 (2004); Sampath, et al., Mol. Cancer Ther., 2(9): 873-74 (2003); and Wolff, et al., Clin. Cancer Res., 9(10): 3589-97 (2003).

The co-administration of taxanes or taxane derivatives with at least one active agent has been reported. Taxotere® in combination with prednisone has been approved by the US Food and Drug Administration for the treatment of metastatic androgen-independent prostate cancer. Rose et al. reported the administration of the oral taxane BMS-275183 in combination with cetuximab (an anti-epidermal growth factor receptor monoclonal antibody) (Rose, et al., Clin. Cancer Res., 10(21): 7413-17 (2004)). Levy, et al. reported the administration of antimetabolite-taxane combinations (specifically, the administration of gemcitabine and docetaxel) in women with anthracycline pretreated metastatic breast cancer (Levy, et al., Cancer Treat. Rev., 31: S17-22 (2005)).

SUMMARY OF THE INVENTION

The invention relates to compositions and methods for treating diseases. In particular aspects, the invention relates to administering a combination of a disintegrin with a small molecule cell division inhibitor for treating cancer. In preferred embodiments, the small molecule cell division inhibitor is a microtubule stabilizing agent. The inventors have discovered that administration of disintegrins in combination with a microtubule stabilizing agent is particularly effective in inhibiting cancer and/or preventing metastasis.

In one aspect, the invention provides a method of treating an individual suffering from cancer, including administering to the individual a therapeutically effective amount of a disintegrin and a microtubule stabilizing agent. In another aspect, the invention provides a method of preventing or inhibiting the growth of metastases in an individual having cancer, the method including administering to the individual an effective amount of a disintegrin and a microtubule stabilizing agent. In yet a further aspect, the invention provides a combination including a therapeutically effective amount of a disintegrin and a microtubule stabilizing agent. In a preferred embodiment, the microtubule stabilizing agent is a taxane.

In some embodiments, the cancer expresses an integrin; preferably, the integrin is αvβ5. In other embodiments, the cancer is one or more cancers selected from the group consisting of prostate cancer, breast cancer, lung cancer, colon cancer, ovarian cancer, renal cancer, central nervous system (CNS) cancer, and leukemia. In a preferred embodiment, the cancer is prostate cancer.

As used herein, "disintegrin" refers to a class of cysteine-rich proteins that are potent soluble ligands of integrins and which are involved in regulating many processes such as cell-cell and cell-extracellular matrix adhesion, migration and invasion, cell cycle progression, differentiation and cell type speciation during development of many metazoan organisms, cell death and apoptosis. The tri-peptide motif RGD (Arg-Gly-Asp) is conserved in most monomeric disintegrins and is located at the tip of a flexible loop, the integrin-binding loop, which is stabilized by disulfide bonds and protruding from the main body of the polypeptide chain. All disintegrins purified from snake venoms bind to the fibrinogen receptor, integrin αIIbβ3, the binding of which results in the inhibition of fibrinogen-dependent platelet aggregation.

Most disintegrins also bind to integrins αvβ3 (a vitronectin receptor) and α5β1 (a fibronectin receptor) in an RGD-dependent manner. Also included within the meaning of disintegrins are biologically active variants and fragments thereof, which variants include for example without limitation, fusion proteins which include disintegrins or fragments thereof In preferred embodiments, the disintegrin is a contortrostatin (CN). CN is a disintegrin isolated from *Agkistrodon contortrix contortrix* (southern copperhead) venom (Trikha, Rote et al. 1994). CN is produced in the snake venom gland as a multidomain precursor of 2027 by having a 1449 bp open reading frame encoding the pro-protein, metalloproteinase and disintegrin domains. The precursor is proteolytically processed, possibly autocatalytically, to generate mature CN. The full length CN proprotein is encoded by the nucleotide sequence 85-1536 of the full length mRNA (GenBank AF212305), whereas the disintegrin domain of CN represents 1339-1533 of the mRNA. The CN disintegrin domain, which contains 65 amino acids, is shown below with the RGD sequence underlined.

(SEQ ID NO: 3)
DAPANPCCDAATCKLTTGSQCADGLCCDQCKFMKEGTVCRRA<u>RGD</u>DLDDY
CNGISAGCPRNPFHA.

Contortrostatin as used herein includes the native homodimer as well as the monomer, precursor or biologically active variant thereof. In some embodiments, the biologically active variant includes an amino acid sequence selected from the group consisting of: (a) amino acid numbers 419 to 483 of SEQ ID NO: 1; (b) amino acid numbers 191 to 410 of SEQ ID NO: 1; (c) amino acid numbers 1 to 190 of SEQ ID NO: 1; (d) SEQ ID NO: 1; (e) an amino acid sequence at least 90% identical to (a), (b) or (d) as determined by FASTA or BLAST using default opening and gap penalties and a default scoring matrix; and (f) an amino acid sequence at least 95% identical to (c) as determined by FASTA or BLAST using default opening and gap penalties and a default scoring matrix.

In certain embodiments, the disintegrin includes a contortrostatin amino acid sequence which is at least 90% percent identical to amino acid numbers 419 to 483 of SEQ ID NO: 1, wherein the contortrostatin amino acid sequence (i) binds to integrin αvβ5 and (ii) induces αvβ3-mediated tyrosine phosphorylation of CAS and FAK in tumor cells.

In yet further embodiments, the disintegrin includes a constrained Arg-Gly-Asp (RGD) sequence of a peptide loop of about 13 amino acid residues flanked by two Cys residues, where the peptide loop is an integrin antagonist which has an amino acid sequence comprising amino acid numbers 457 to 469 of SEQ ID NO: 1.

In other embodiments, the disintegrin is vicrostatin, which is a fusion protein that includes a contortrostatin domain N-terminal to the sequence HKGPAT (SEQ ID NO: 47):

As used herein, the term "purified" in reference to polypeptides (or proteins) does not require absolute purity. Instead, it represents an indication that the polypeptide(s) of interest is(are) in an environment in which the protein is more abundant (on a mass basis) than the environment from which the protein was initially produced. Purified polypeptides may be obtained by a number of methods including, for example, chromatography, preparative electrophoresis, centrifugation, precipitation, affinity purification, etc. The degree of purity is preferably at least 10%. One or more "substantially purified" polypeptides are at least 50% of the protein content of the environment, more preferably at least 75% of the protein content of the environment, and most preferably at least 95% of the protein content of the environment. Protein content may be determined using a modification of the method of Lowry, et al. (Lowry, Rosebrough et al. 1951), described by Hartree (Hartree 1972), using bovine serum albumin as a protein standard.

As described herein, cancer therapy is achieved by administering a combination of a disintegrin with an agent that inhibits cell division. Preferably, the cell division inhibitor is a microtubule stabilizing agent.

As used herein, "microtubule stabilizing agent" refers to any compound which inhibits cell division by binding to B tubulin and thereby disrupting the equilibrium between the free β tubulin and microtubules (See e.g., Pamela et al., Clin Cancer Res Vol. 8, 846-855 (2002)). Stabilization of microtubules by a microtubule stabilizing agents causes mitotic arrest and cell death (e.g., apoptosis). At certain doses, microtubule stabilizing agents may have other effects including induction of genes encoding inflammatory mediators such as tumor necrosis factor alpha, interleukins, and enzymes such as NO synthase and COX-2. Microtubule stabilizing agents are preferably small molecules of 1,500 daltons or less, preferably 1,000 daltons or less. Exemplary microtubule stabilizing agents include, but are not limited to, taxanes and non-taxanes such as epothilones.

"Taxane" refers to a chemical class of diterpenoids compounds that inhibit cell division. Taxanes as used herein share a common core structure (i.e., a taxoid core) shown below.

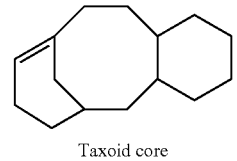

Taxoid core

Taxol® (paclitaxel), and Taxotere® (docetaxel) are well known microtubule stabilizing agents of the taxane family. The term "taxane" as used herein also encompasses derivatives of naturally occurring taxanes referred to herein as a "taxane derivative" or "taxoid analog." A preferred taxane is shown in Formula I.

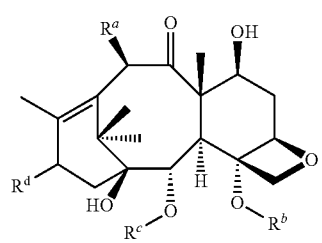

Formula I wherein:
  $R^a$ is hydrogen, hydroxyl, alkyl, substituted alkyl, oxy, substituted oxy, cycloalkyl, substituted cycloalkyl, heterocycloalkyl, substituted heterocycloalkyl, aryl, substituted aryl, heteroaryl, substituted heteroaryl, or —C(O)$R^e$;
  $R^b$ is hydrogen, alkyl, substituted alkyl, or C(O)$R^e$;
  $R^c$ is hydrogen, alkyl, substituted alkyl, aryl, substituted aryl, heteroaryl, substituted heteroaryl, or C(O)$R^e$;
  $R^d$ is alkyl, alkenyl, cycloalkyl, heterocycloalkyl, aryl, heteroaryl, alkoxy, alkenoxy, or —OC(O)$R^e$, each of which may be optionally substituted;

$R^e$ is hydrogen, alkyl, alkenyl, amino, cycloalkyl, heterocycloalkyl, aryl, heteroaryl or —(CH$_2$)$_n$NHC(O)R$^f$, each of which may be optionally substituted; and R$^f$ is alkyl, alkenyl, oxy, cycloalkyl, heterocycloalkyl, aryl, or heteroaryl, each of which may be optionally substituted;

wherein n is an integer between 1 and 5.

In particular embodiments, the taxane has the structure shown as Formula II.

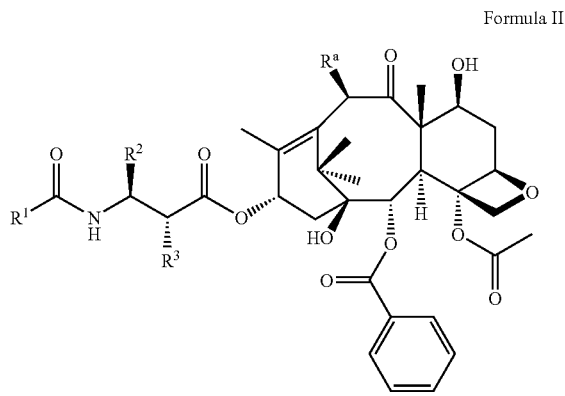

Formula II wherein:
R$^1$ and R$^2$ are independently selected from alkyl, alkenyl, cycloalkyl, heterocycloalkyl, aryl, heteroaryl, or oxy, each of which may be optionally substituted;

R$^3$ and R$^4$ are independently selected from alkyl, substituted alkyl, hydroxyl, oxy, C(O)H, or OC(O)R$^5$; and R$^5$ is alkyl, alkenyl, cycloalkyl, heterocycloalkyl, aryl, or heteroaryl, each of which may be optionally substituted.

In other embodiments, the taxane has the structure shown as Formula III.

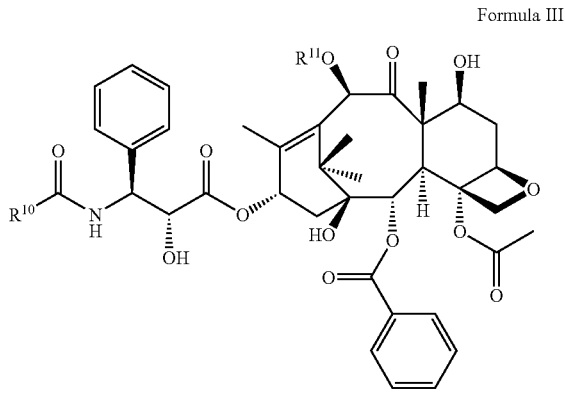

Formula III wherein
R$^{10}$ is selected from alkyl, cycloalkyl, aryl or heteroaryl, each of which may be optionally substituted; and R$^{11}$ is selected from hydrogen, alkyl, —C(O)H, —C(O)CH$_3$, or —C(O)CH$_2$CH$_3$.

In further embodiments of Formula III, R$^{10}$ is selected from —C(CH$_3$)$_3$ or phenyl and R$^{11}$ is selected from hydrogen, —C(O)CH$_3$ or —C(O)CH$_2$CH$_3$. In a one embodiment, R$^{10}$ is —C(CH$_3$)$_3$ and R$^{11}$ is H. In another embodiment, R$^{10}$ is phenyl and R$^{11}$ is —C(O)CH$_3$.

Also included within the meaning of "taxane" as used herein are rearranged taxoids having the structure shown in Formula IV, which are described, for example, in Choudhary, et al., Chem. Pharm. Bull., 50(11): 1488-90 (2002). Rearranged taxoids useful in the invention are microtubule stabilizing agents.

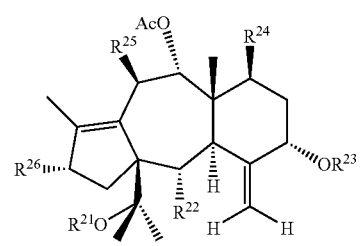

Formula IV wherein
R$^{21}$ and R$^{23}$ are independently selected from hydrogen, lower alkyl, substituted lower alkyl, acetyl, cycloalkyl, substituted cycloalkyl, aryl, substituted aryl, heteroaryl or substituted heteroaryl;

R$^{22}$ is selected from hydrogen, hydroxy, lower alkyl, substituted lower alkyl or acetyl;

R$^{24}$, R$^{25}$ and R$^{26}$ are each independently selected from hydrogen, hydroxy, lower alkyl, substituted lower alkyl, oxy, acetyl, cycloalkyl, substituted cycloalkyl, heterocycloalkyl, substituted heterocycloalkyl, aryl, substituted aryl, heteroaryl, or substituted heteroaryl.

In further embodiments of Formula IV, R$^{21}$ is acetyl, R$^{22}$ is acetyl, R$^{23}$ and R$^{26}$ are hydrogen and R$^{24}$ and R$^{25}$ are hydroxy. In other embodiments, R$^{21}$, R$^{22}$ and R$^{24}$ are each hydrogen, and R$^{23}$, R$^{25}$ and R$^{26}$ are each —C(O)OCH$_3$.

In preferred embodiments, the taxanes including those of Formulas I-III are administered in combination with a disintegrin, preferably contortrostatin. In preferred embodiments, the taxanes including Formulas I-III are administered in combination with vicrostatin.

In another aspect of the present invention, a non-taxane microtubule stabilizing agent having the structure shown in Formula V is administered in combination with a disintegrin:

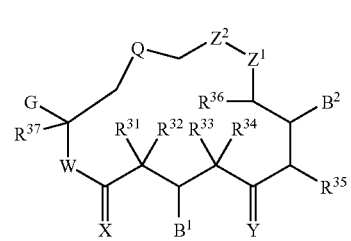

Formula V wherein
Q is selected from the group consisting of

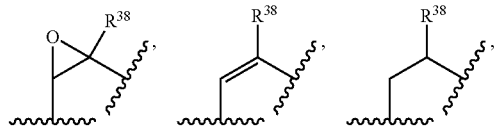

-continued

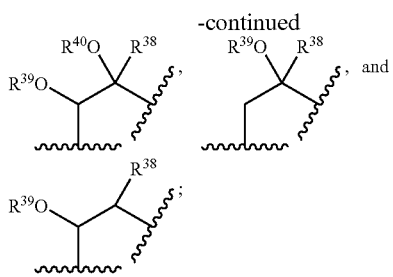

G is selected from the group consisting of alkyl, substituted alkyl, substituted or unsubstituted aryl, heterocyclo,

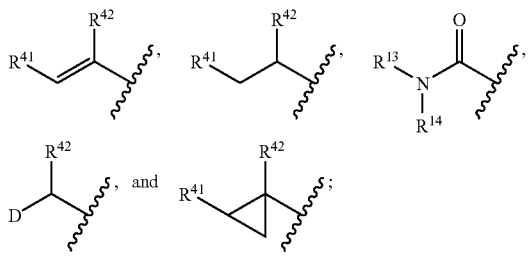

W is O or $NR^{45}$;
X is O or H, H;
Y is selected from the group consisting of O; H, $OR^{46}$; $OR^{47}$, $OR^{47}$; $NOR^{48}$; H, $NOR^{49}$; H, $NR^{50}R^{51}$; H, H; and $CHR^{52}$; wherein $OR^{47}$ $OR^{47}$ can be a cyclic ketal;
$Z^1$ and $Z^2$ are independently selected from the group consisting of $CH_2$, O, $NR^{53}$, S and $SO_2$, wherein only one of $Z^1$ and $Z^2$ can be a heteroatom;
$B^1$ and $B^2$ are independently selected from the group consisting of $OR^{54}$, $OC(O)R^{55}$, and $OC(O)NR^{56}R^{57}$; wherein when $B^1$ is OH and Y is OH, H, $B^1$ and Y can form a six-membered ring ketal or acetal;
D is selected from the group consisting of $NR^{58}R^{59}$, $NR^{60}COR^{61}$ and saturated heterocycle;
$R^{31}$, $R^{32}$, $R^{33}$, $R^{34}$, $R^{35}$, $R^{36}$, $R^{37}$, $R^{48}$, $R^{49}$, $R^{50}$, $R^{51}$, $R^{52}$, $R^{56}$ and $R^{57}$ are independently selected from H, alkyl, substituted alkyl, or aryl, wherien when $R^{31}$ and $R^{32}$ are alkyl, they can be joined to form a cycloalkyl; and when $R^{33}$ and $R^{34}$ are alkyl, they can be joined to form a cycloalkyl;
$R^{39}$, $R^{40}$, $R^{46}$ and $R^{47}$ are independently selected from H, alkyl, and substituted alkyl;
$R^{38}$, $R^{41}$, $R^{42}$, $R^{58}$, $R^{60}$, $R^{62}$ and $R^{63}$ are independently selected from the group consisting of H, alkyl, substituted alkyl, aryl, substituted aryl, cycloalkyl, and heterocyclo;
$R^{13}$, $R^{14}$ and $R^{61}$ are independently selected from the group consisting of H, alkyl, substituted alkyl, aryl, heteroaryl, cycloalkyl, and heterocyclo;
$R^{54}$ and $R^{55}$ are independently selected from the group consisting of H, alkyl, substituted alkyl, aryl, substituted aryl, and heterocyclo;
$R^{45}$, $R^{53}$ and $R^{59}$ are independently selected from the group consisting of H, alkyl, substituted alkyl, aryl, substituted aryl, cycloalkyl, heterocyclo, $R^{62}C(O)$, $R^{63}SO_2$, hydroxy, O-alkyl and O-substituted alkyl;
and any salts, solvates or hydrates thereof
In one embodiment, Y and X are O; W is O or NH; $B^1$ and $B^2$ are OH; $R^{31}$ and $R^{32}$ are H; $R^{33}$ $R^{34}$ and $R^{36}$ are $CH_3$; $Z^1$ and $Z^2$ are CH; and G is $—R^gR^h$ wherein $R^g$ is lower alkyl or lower alkenyl and $R^h$ is an optionally substituted herteroaryl or heterocycle. In one embodiment, the disintegrin is contortrostatin. In another embodiment, the disintegrin is vicrostatin.

In yet another aspect of the present invention, a non-taxane microtubule stabilizing agent having the structure shown in Formula Va is administered in combination with a disintegrin:

Formula Va

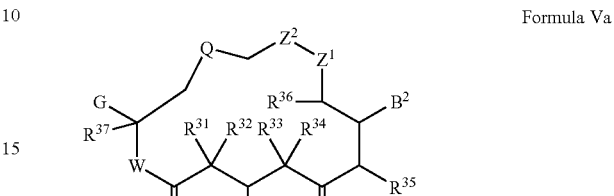

wherein
Q is selected from the group consisting of

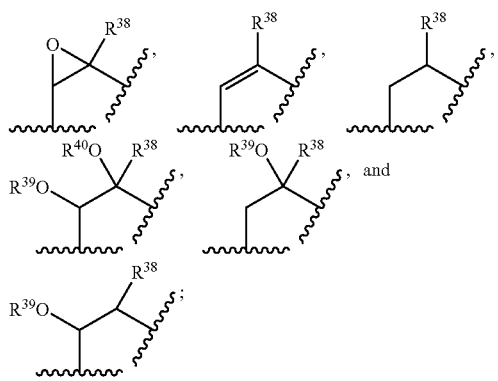

G is selected from the group consisting of alkyl, substituted alkyl, substituted or unsubstituted aryl, heterocyclo,

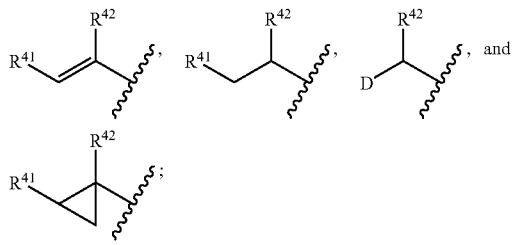

W is O or $NR^{45}$;
X is O or H, H;
Y is selected from the group consisting of O; H, $OR^{46}$; $OR^{47}$, $OR^{47}$; $NOR^{48}$; H, $NOR^{49}$; H, $NR^{50}R^{51}$; H, H; and $CHR^{52}$; wherein $OR^{47}$ $OR^{47}$ can be a cyclic ketal;
$Z^1$ and $Z^2$ are independently selected from the group consisting of $CH_2$, O, $NR^{53}$, S and $SO_2$, wherein only one of $Z^1$ and $Z^2$ can be a heteroatom;
$B^1$ and $B^2$ are independently $OC(O)NR^{56}R^{57}$;
D is selected from the group consisting of $NR^{58}R^{59}$ and saturated heterocycle;
$R^{31}$, $R^{32}$, $R^{33}$, $R^{34}$, $R^{35}$, $R^{36}$, $R^{37}$, $R^{48}$, $R^{49}$, $R^{50}$, $R^{51}$, $R^{52}$, $R^{56}$ and $R^{57}$ are independently selected from H, alkyl, substituted alkyl, or aryl, wherein when $R^{31}$ and $R^{32}$ are alkyl, they can be joined to form a cycloalkyl; and when $R^{33}$ and $R^{34}$ are alkyl, they can be joined to form a cycloalkyl;

$R^{39}$, $R^{40}$, $R^{46}$ and $R^{47}$ are independently selected from H, alkyl, and substituted alkyl;

$R^{38}$, $R^{41}$, $R^{42}$, $R^{58}$, $R^{62}$ and $R^{63}$ are independently selected from the group consisting of H, alkyl, substituted alkyl, aryl, substituted aryl, cycloalkyl, and heterocyclo;

$R^{45}$, $R^{53}$ and $R^{59}$ are independently selected from the group consisting of H, alkyl, substituted alkyl, aryl, substituted aryl, cycloalkyl, heterocyclo, $R^{62}C(O)$, $R^{63}SO_2$, hydroxy, O-alkyl and O-substituted alkyl;

and any salts, solvates or hydrates thereof

In another aspect of the present invention, a non-taxane microtubule stabilizing agent having the structure shown in Formula VI is administered in combination with a disintegrin.

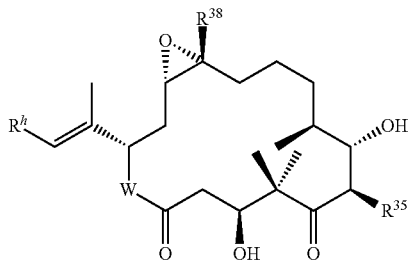

Formula VI wherein W is O, NH or $NR^{64}$;

$R^{35}$ and $R^{38}$ are independently selected from lower alkyl or lower alkenyl;

$R^{64}$ is selected from H, OH, optionally substituted alkyl, optionally substituted oxy, optionally substituted cycloalkyl, optionally substituted heterocycloalkyl, optionally substituted aryl, or optionally substituted heteroaryl; and $R^h$ is selected from cycloalkyl, heterocycloalkyl, aryl or heteroaryl, each of which may be optionally substituted.

In one embodiment, W is O or NH; $R^{35}$ and $R^{38}$ are $CH_3$, and $R^h$ is selected from a substituted thiazole, oxazole or pyridine. In another embodiment, the disintegrin is contortrostatin. In another embodiment, the disintegrin is vicrostatin.

"Halo" and "halogen" refer to all halogens, that is, chloro (Cl), fluoro (F), bromo (Br), or iodo (I).

"Hydroxyl" and "hydroxy" refer to the group OH.

"Oxy" refers to the group OR, where R can be alkyl, acyl, aryl, heteroaryl, aralkyl, cycloalkyl, or heterocyclyl.

"Substituted oxy" refers to the group OR, where R can be substituted alkyl, substituted acyl, substituted aryl, substituted heteroaryl, substituted aralkyl, substituted cycloalkyl or substituted heterocyclyl.

"Alkoxy" refers to the group $OR^{cc}$, where $R^{cc}$ is alkyl, wherein alkyl is as defined herein.

"Substituted alkoxy" refers to the group $OR^{dd}$, where $R^{dd}$ is an alkyl group as defined herein, substituted with one or more groups or substituents such as halo, hydroxy, oxy, amino, alkylamino, arylamino, aralkylamino, cycloalkylamino, or heterocycloamino.

"Alkyl" refers to an alkane-derived radical containing from 1 to 20, preferably 1 to 8, more preferably 1-4, yet more preferably 1-2, carbon atoms. Alkyl includes straight chain alkyl, and branched alkyl such as methyl, ethyl, propyl, isopropyl, butyl, t-butyl, and the like, as well as cycloalkyl as defined herein. The alkyl group can be attached at any available point to produce a stable compound.

"Substituted alkyl" is an alkyl group independently substituted with one or more, e.g., 1, 2, or 3, groups or substituents such as halo, trifluoromethyl, trifluoromethoxy, hydroxy, alkoxy, cycloalkyoxy, heterocylooxy, oxo, alkanoyl, aryloxy, alkanoyloxy, amino, alkylamino, arylamino, aralkylamino, cycloalkylamino, heterocycloamino, disubstituted amines in which the 2 amino substituents are selected from alkyl, aryl or aralkyl, alkanoylamino, aroylamino, aralkanoylamino, substituted alkanoylamino, substituted arylamino, substituted aralkanoylamino, thiol, alkylthio, arylthio, aralkylthio, cycloalkylthio, heterocyclothio, alkylthiono, arylthiono, aralkylthiono, alkylsulfonyl, arylsulfonyl, aralkylsulfonyl, sulfonamido (e.g. $SO_2$, $NH_2$), substituted sulfonamido, nitro, cyano, carboxy, carbamyl (e.g. $CONH_2$), substituted carbamyl (e.g. CONH alkyl, CONH aryl, CONH aralkyl or cases where there are two substituents on the nitrogen selected from alkyl, aryl or aralkyl), alkoxycarbonyl, aryl, substituted aryl, guanidino and heterocyclos, such as, indolyl, imidazolyl, furyl, thienyl, thiazolyl, pyrrolidyl, pyridyl, pyrimidyl and the like. Where noted above where the substituent is further substituted it will be with halogen, alkyl, alkoxy, aryl or aralkyl.

"Lower alkyl" refers to an alkyl group having 1-6 carbon atoms.

"Substituted lower alkyl" is a lower alkyl which is substituted with one or more, e.g., 1, 2, or 3, groups or substituents, as defined above, attached at any available point to produce a stable compound.

"Aryl" means a monocyclic or bicyclic aromatic hydrocarbon group having 6 to 12 carbon atoms in the ring portion, such as phenyl, naphthyl, biphenyl and diphenyl groups.

"Substituted aryl" refers to an aryl group as defined above independently substituted with one or more, e.g., 1, 2, or 3, groups or substituents such as halo, hydroxy, optionally substituted alkoxy, optionally substituted alkylthio, alkylsulfinyl, alkylsulfonyl, optionally substituted amino, optionally substituted amido, amidino, urea optionally substituted with alkyl, aminosulfonyl optionally N-mono- or N,N-di-substituted with alkyl, alkylsulfonylamino, carboxyl, heterocycle, substituted heterocycle, nitro, cyano, thiol, sulfonylamino, or the like, attached at any available point to produce a stable compound.

"Aralkyl" refers to an aryl substituted alkyl group, such as benzyl.

"Cycloalkyl" refers to optionally substituted, saturated cyclic hydrocarbon ring systems, preferably containing 1 to 3 rings and 3 to 10 carbons per ring which may be further fused with an unsaturated $C_3$-$C_7$ carbocyclic ring. Exemplary groups include cyclopropyl, cyclobutyl, cyclopentyl, cyclohexyl, cycloheptyl, cyclooctyl, cyclodecyl, cyclododecyl, and adamantyl. Exemplary substituents include one or more alkyl groups as described above, or one or more groups described above as alkyl substituents.

The terms "heterocycle", "heterocyclic" and "heterocyclo" refer to an optionally substituted, fully saturated or unsaturated, aromatic or nonaromatic cyclic group, for example, which is a 4 to 7 membered monocyclic, 7 to 11 membered bicyclic, or 10 to 15 membered tricyclic ring system, which has at least one heteroatom in at least one carbon atom-containing ring. Each ring of the heterocyclic group containing a heteroatom may have 1, 2 or 3 heteroatoms selected from nitrogen atoms, oxygen atoms and sulfur atoms, where the nitrogen and sulfur heteroatoms may also optionally be oxidized and the nitrogen heteroatoms may also optionally be quaternized. The heterocyclic group may be attached at any heteroatom or carbon atom.

The term "heteroatoms" includes oxygen, sulfur and nitrogen.

Exemplary monocyclic heterocyclic groups include pyrrolidinyl, pyrrolyl, indolyl, pyrazolyl, oxetanyl, pyrazolinyl, imidazolyl, imidazolinyl, imidazolidinyl, oxazolyl, oxazolidinyl, isoxazolinyl, isoxazolyl, thiazolyl, thiadiazolyl, thiazolidinyl, isothiazolyl, isothiazolidinyl, furyl, tetrahydrofuryl, thienyl, oxadiazolyl, piperidinyl, piperazinyl, 2-oxopiperazinyl, 2-oxopiperidinyl, 2-oxopyrrolidinyl, 2-oxazepinyl, azepinyl, 4-piperidonyl, pyridyl, N-oxo-pyridyl, pyrazinyl, pyrimidinyl, pyridazinyl, tetrahydropyranyl, tetrahydrothiopyranyl, tetrahydrothiopyranyl sulfone, morpholinyl, thiomorpholinyl, thiomorpholinyl sulfoxide, thiomorpholinyl sulfone, 1,3-dioxolane and tetrahydro-1,1-dioxothienyl, dioxanyl, isothiazolidinyl, thietanyl, thiiranyl, triazinyl, and triazolyl, and the like.

Exemplary bicyclic heterocyclic groups include benzothiazolyl, benzoxazolyl, benzothienyl, quinuclidinyl, quinolinyl, quinolinyl-N-oxide, tetrahydroisoquinolinyl, isoquinolinyl, benzimidazolyl, benzopyranyl, indolizinyl, benzofuryl, chromonyl, coumarinyl, cinnolinyl, quinoxalinyl, indazolyl, pyrrolopyridyl, furopyridinyl (such as furo[2,3-c]pyridinyl, furo[3,1-b]pyridinyl] or furo[2,3-b]pyridinyl), dihydroisoindolyl, dihydroquinazolinyl (such as 3,4-dihydro-4-oxo-quinazolinyl), benzisothiazolyl, benzisoxazolyl, benzodiazinyl, benzofurazanyl, benzothiopyranyl, benzotriazolyl, benzpyrazolyl, dihydrobenzofuryl, dihydrobenzothienyl, dihydrobenzothiopyranyl, dihydrobenzothiopyranyl sulfone, dihydrobenzopyranyl, indolinyl, isochromanyl, isoindolinyl, naphthyridinyl, phthalazinyl, piperonyl, purinyl, pyridopyridyl, quinazolinyl, tetrahydroquinolinyl, thienofuryl, thienopyridyl, thienothienyl, and the like.

Exemplary substituents include one or more alkyl groups as described above or one or more groups described above as alkyl substituents. Also included are smaller heterocyclos, such as, epoxides and aziridines.

"Amino" or "amine" denotes the group —NH$_2$. A "disubstituted amine" denotes ——NR$_2$ where R is lower alkyl, aryl, substituted aryl, heteroaryl, substituted heteroaryl, acyl, substituted acyl, sulfonyl or substituted sulfonyl.

"Alkenyl" refers to a straight chain, branched, or cyclic hydrocarbon containing 2-20, preferably 2-17, more preferably 2-10, even more preferably 2-8, most preferably 2-4, carbon atoms, and which contains at least one, preferably 1-3, more preferably 1-2, and most preferably one, carbon to carbon double bond. In the case of a cycloalkyl group, conjugation of more than one carbon to carbon double bond is not such as to confer aromaticity to the ring. Carbon to carbon double bonds may be either contained within a cycloalkyl portion, or within a straight chain or branched portion. Examples of alkenyl groups include, but are not limited to, ethenyl, propenyl, isopropenyl, butenyl, cyclohexenyl, cyclohexenylalkyl, and the like.

"Substituted alkenyl" is an alkenyl which is independently substituted with one or more, e.g., 1, 2, or 3, groups or substituents such as halo, hydroxy, optionally substituted alkoxy, optionally substituted alkylthio, alkylsulfinyl, alkylsulfonyl, acyloxy, optionally substituted aryl, optionally substituted aryloxy, optionally substituted heteroaryloxy, optionally substituted amino, optionally substituted amido, amidino, urea optionally substituted with alkyl, aryl, heteroaryl or heterocyclyl groups, aminosulfonyl optionally N-mono- or N,N-di-substituted with alkyl, aryl or heteroaryl groups, alkylsulfonylamino, arylsulfonylamino, heteroarylsulfonylamino, alkylcarbonylamino, arylcarbonylamino, heteroarylcarbonylamino, carboxyl, heterocycle, substituted heterocycle, heteroaryl, substituted heteroaryl, nitro, cyano, thiol, sulfonylamino or the like attached at any available point to produce a stable compound.

"Lower alkenyl" refers to an alkenyl group having 1-6 carbon atoms.

"Substituted lower alkenyl" is a lower alkenyl which is substituted with 1 or more, e.g., 1, 2, or 3, groups or substituents such as halo, hydroxy, optionally substituted alkoxy, optionally substituted alkylthio, alkylsulfinyl, alkylsulfonyl, acyloxy, optionally substituted aryl, optionally substituted aryloxy, optionally substituted heteroaryloxy, optionally substituted amino, optionally substituted amido, amidino, urea optionally substituted with alkyl, aryl, heteroaryl or heterocyclyl groups, aminosulfonyl optionally N-mono- or N,N-di-substituted with alkyl, aryl or heteroaryl groups, alkylsulfonylamino, arylsulfonylamino, heteroarylsulfonylamino, alkylcarbonylamino, arylcarbonylamino, heteroarylcarbonylamino, carboxyl, heterocycle, substituted heterocycle, heteroaryl, substituted heteroaryl, nitro, cyano, thiol, sulfonylamino or the like attached at any available point to produce a stable compound.

In another aspect of the present invention, an individual suffering from cancer is treated by administering an effective amount of a disintegrin in combination with an effective amount of at least one microtubule stabilizing agent. In one embodiment, the disintegrin is selected from contortrostatin or vicrostatin. In another embodiment, an effective amount of a disintegrin in administered in combination with an effective amount of a taxane microtubule stabilizing agent and an effective amount of a non-taxane microtubule stabilizing agent.

In one aspect of the present invention, the disintegrin is administered before the microtubule stabilizing agent. In another aspect, the disintegrin is administered after the microtubule stabilizing agent. In yet another aspect, the disintegrin and microtubule stabilizing agent are co-administered.

In accordance with the methods of the invention, the disintegrin and microtubule stabilizing agent may be co-administered, or administered separately in any order. Co-administration refers to simultaneous delivery of two or more drugs. Treatment which combines administration of a disintegrin and a microtubule stabilizing agent, if co-administered, is preferably administered so that both drugs are in the body in active form at the same time.

In accordance with the methods of the invention, treatment with a disintegrin and microtubule stabilizing agent may be repeated at later times. Multiple treatments are likely to be necessary in most instances. When repeat administrations are used, the disintegrin and the microtubule stabilizing agent need not be administered an equal number of times. In addition, the dose of the disintegrin and the microtubule stabilizing agent may be modified for repeat administrations as medically required.

As used herein, "treating" refers to the administration of an agent (for example a disintegrin or a microtubule stabilizing agent) to a subject. Although it is preferred that treating a condition such as cancer will result in an improvement of the condition, the term treating as used herein does not indicate, imply, or require that the administration of the agent is successful in reducing or ameliorating symptoms associated with any particular condition. In some individuals, a treatment may result in adverse effects or even worsen a condition which the treatment was intended to improve.

As used herein, "administration" or "administer" or "administering" refers to dispensing, applying, or tendering an agent (for example a disintegrin or taxane) to a subject. Administration may be performed using any of a number of methods known in the art.

As used herein, "effective amount" refers to a dose sufficient to provide a concentration high enough to impart a beneficial effect on the recipient thereof. An "effective amount" is that which is determined by conducting clinical trials in accordance with generally accepted or legal guidelines. The specific therapeutically effective dose level for any particular subject will depend upon a variety of factors including the disorder being treated, the severity of the disorder, the activity of the specific compound, the route of administration, the rate of clearance of the compound, the duration of treatment, the drugs used in combination or coincident with the compound, the age, body weight, sex, diet and general health of the subject, and like factors well known in the medical arts and sciences. Various general considerations taken into account in determining the "therapeutically effective amount" are known to those of skill in the art and are described, e.g., in Gilman et al., eds., Goodman And Gilman's: The Pharmacological Bases of Therapeutics, 8th ed., Pergamon Press, 1990; and Remington's Pharmaceutical Sciences, 17th ed., Mack Publishing Co., Easton, Pa., 1990.

As used herein, "composition" refers to a formulation suitable for administration to an intended animal subject for therapeutic purposes that contains at least one pharmaceutically active compound and at least one pharmaceutically acceptable carrier or excipient. The term "pharmaceutically acceptable" indicates that the identified material does not have properties that would cause a reasonably prudent medical practitioner to avoid administration of the material to a patient, taking into consideration the disease or conditions to be treated and the respective route of administration. For example, it is commonly required that such a material be essentially sterile, e.g., for injectibles. Techniques for formulation and administration may be found, for example, in "Remington's Pharmaceutical Sciences," (18th ed., Mack Publishing Co., Easton Pa., 1990).

As used herein, "about" means in quantitative terms plus or minus 10%.

As used herein, "analog" means a compound that resembles another in structure but differs by at least one atom.

As used herein, "combination" refers to any association between or among two or more items. The combination can be two or more separate items, such as two compositions or two collections. It can be a mixture thereof, such as a single mixture of the two or more items, or any variation thereof.

As used herein "derivative" is a chemical substance derived from another substance by modification or substitution.

BRIEF DESCRIPTION OF THE FIGURES

FIG. 2 shows the amino acid sequence of contortrostatin (SEQ ID NO:1).

FIG. 3 shows the full-length nucleotide sequence of contortrostatin cDNA (SEQ ID NO:2).

DETAILED DESCRIPTION OF THE INVENTION

Figure 1:
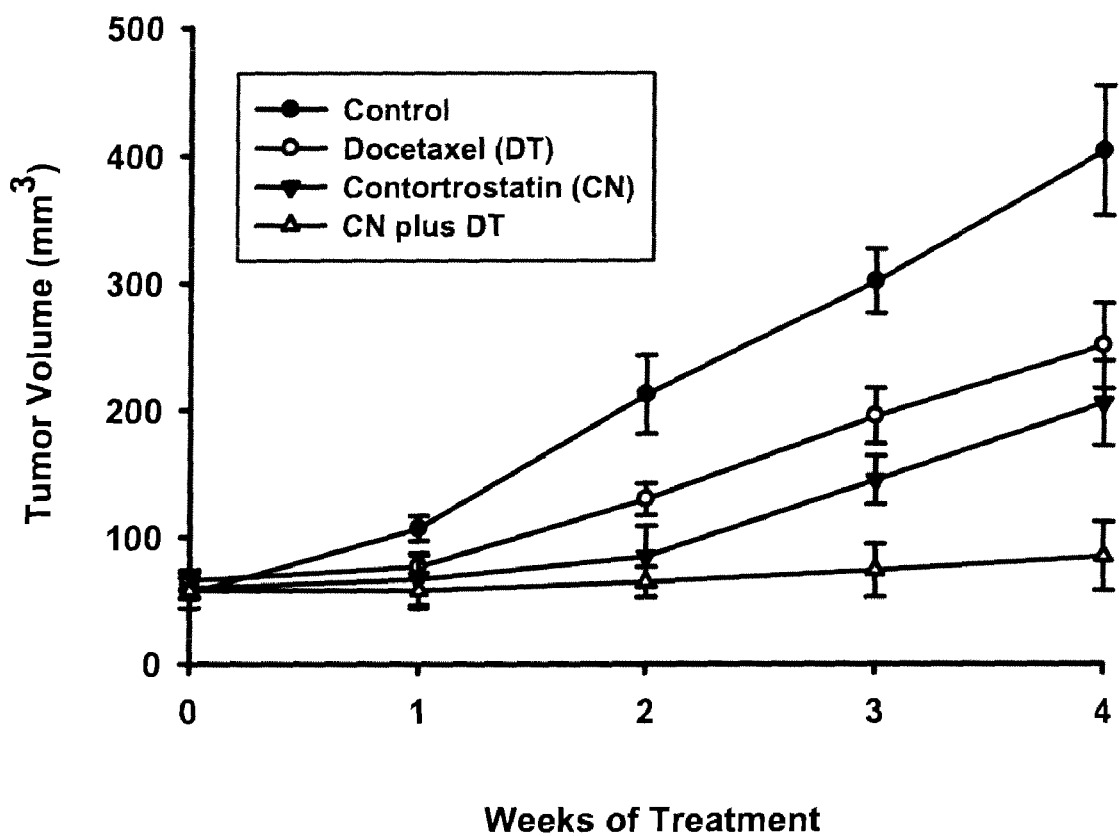
FIG. 1 shows the inhibition of PC-3 xenograft tumor growth of four treatment groups. Mice were treated with either PBS, CN, docetaxel, or CN plus docetaxel. The group that received a combination of CN and docetaxel resulted in the greatest inhibition of tumor growth. Error bars represent SEM. Experimental details are described in Example 7.

The invention relates to compositions and methods for treating cancer. In particular aspects, the invention relates to administering a combination of a disintegrin with a microtubule stabilizing agent useful for treatment of cancer. The methods and compositions of the invention are useful for inhibiting the growth of a cancer or inhibiting the emergence or growth of metastases. The invention methods and compositions are particularly suited for inhibiting the appearance or growth of cancer metastatic to the bone such as in cases of breast and prostate cancer.

Prostate cancer is a major public health issue. With the exception of skin cancer, prostate cancer is the most prevalent cancer in American men and the second leading cause of cancer death. American Cancer Society data indicated 220,900 men diagnosed with and 28,900 deaths from prostate cancer in the United States in 2005. Despite improvements in diagnosis, surgical techniques, and local and systemic adjuvant therapies, most deaths from prostate cancer are still caused by metastases, especially to the bones, that are resistant to conventional therapies. Osteoblastic metastases are common in lethal prostate cancer.

The therapeutic efficacy of CN has been proven in a subcutaneous human prostate cancer nude mouse model. See Pinski, et al., Proc. Am. Soc. Clin. Oncol. 22: 218 (2003) (abstr 874). In one aspect of the invention, contortrostatin (CN) is combined with a taxane for inhibiting tumor growth and appearance or growth of metastases.

Preparation of Disintegrin

Disintegrins may be obtained by purifying them from natural sources such as snake venom using methods well known in the art. For example, the purification of contortrostatin from *Agkistrodon contortrix contortrix* (Southern copperhead) venom using a four step HPLC procedure is described in U.S. Pat. No. 5,731,288 (Markland, et al.). Also described therein are methods to characterize the purified disintegrin such as SDS-polyacrylamide gel electrophoresis (SDS-PAGE), mass spectrometry, Scatchard analysis of binding to unactivated human platelets to determine the $IC_{50}$ of the preparation.

Disintegrins also may be obtained by synthetic methods or by recombinant expression techniques. In this regards, U.S. Pat. No. 6,710,030 (Markland et al.) discloses the nucleotide and amino acid sequence of native contortrostatin which results from proteolytic processing of a contortrostatin precursor. The precursor is a multidomain protein that includes pro-protein, metalloproteinase, and disintegrin (mature contortrostatin) domains. U.S. Pat. No. 6,710,030 also describes various biologically active variants and fragments of contortrostatin.

Methods of expressing disintegrins by recombinant means in prokaryotic organisms is described in international Application Serial No. PCT/US2006/004413 (see also U.S. application Ser. No. 11/351,311), filed Feb. 9, 2006. As described therein, expression of the disintegrin in prokaryotic host cells is achieved by expressing as a genetic fusion a bacterial thioredoxin such as thioredoxin A (TrxA). This is achieved by cloning DNA sequence encoding the disintegrin downstream (i.e., 3') to sequence encoding the thioredoxin. This can be cloned into a suitable expression vector such as pET32a.

An exemplary thioredoxin is thioredoxin A (TrxA) from *E. coli*, which is about 109 amino acids in length and is encoded by the trxA gene. The amino acid sequence of *E. coli* wild type thioredoxin A is shown below with the active site CXXC bolded and underlined.

(SEQ ID NO: 4)
MSDKIIHLTDDSFDTDVLKADGAILVDFWAEWCGPCKMIAPILDEIADE

YQGKLTVAKLNIDQNPGTAPKYGIRGIPTLLLFKNGEVAATKVGALSKG

QLKEFLDANLA.

Active site mutants of thioredoxin may be used in place of wild type thioredoxin in the fusion protein. Thus, thioredoxin active-site motif CXXC can be replaced with an active-site motif from another oxido-reductase. For example, active site mutants of wild type thioredoxin A may be used in place of wild type thioredoxin in the fusion construct with the eukaryotic protein. In this regard, thioredoxin A's active site motif CGPC (SEQ ID NO: 48) may be replaced with the active site motif CPYC (SEQ ID NO: 49), taken from another bacterial oxido-reductase, glutaredoxin A (also called glutaredoxin 1). This mutant may be referred to as a glutaredoxin-like thioredoxin. Another thioredoxin active site mutant is the PDI-like thioredoxin, generated by replacing the active site wild type motif CGPC (SEQ ID NO: 48) with the active site motif CGHC (SEQ ID NO: 50), taken from eukaryotic protein disulfide isomerase (PDI).

Also described in PCT/US2006/004413 is to transform the disintegrin expression vector into prokaryotic host cells that have been are engineered in ways to enhance expression of proteins with large numbers of disulfide bridging such as disintegrins. Host cell engineering includes cytoplasmic expression of a disulfide isomerase (such as DsbC) normally targeted to the periplasmic space in bacteria and/or cytoplasmic expression of a redox catalyst such as the á-domain of the bacterial thiol-disulfide interchange protein DsbD also normally targeted to the periplasmic space. Cytoplasmic localization of DsbC or the α-domain of DsbD can be achieved by expressing the mature protein without a signal sequence. PCT/US2006/004413 also describes active site mutants of DsbC that have increased isomerase activity. This may be achieved by replacing the *E. coli* wildtype sequence CGYC (SEQ ID NO: 51) with CGFC (SEQ ID NO: 52) or CTFC (SEQ ID NO: 53).

The sequence of *E. coli* DsbC is shown below without the signal sequence and with the active site CGYC (SEQ ID NO: 51) underlined and bolded.

```
                                        (SEQ ID NO: 5)
DDAAIQQTLAKMGIKSSDIQPAPVAGMKTVLTNSGVLYITDDGKHIIQGP

MYDVSGTAPVNVTNKMLLKQLNALEKEMIVYKAPQEKHVITVFTDITCGY

CHKLHEQMADYNALGITVRYLAFPRQGLDSDAEKEMKAIWCAKDKNKAFD

DVMAGKSVAPASCDVDIADHYALGVQLGVSGTPAVVLSNGTLVPGYQPPK

EMKEFXDEHQKMTSGK
```

The DsbD α-domain represents the first 132 amino acids of mature DsbD from which a cleavable signal sequence of 19 aa is removed. The sequence of the DsbD α-domain without the leader sequence and with the catalytic site underlined is shown below.

```
                                        (SEQ ID NO: 6)
GLFDAPGRSQFVPADQAFAFDFQQNQHDLNLTWQIKDGYYLYRKQIRITP

EHAKIADVQLPQGVWHEDEFYGKSEIYRDRLTLPVTINQASAGATLTVTY

QGCADAGFCYPPETKTVPLSEVVANNEASQPV
```

PCT/US2006/004413 also describes other useful bacterial host cell mutants including a mutant trxB gene and/or a mutant gor gene, rendering the cell deficient in thioredoxin reductase activity and/or glutathione reductase activity. Other host cell mutations include deficiency in one or more proteases such as those encloded by ompT and lon genes. For example, *E. coli* host cells AD494(DE3)pLysS are deficient in trxB gene as well as ompT and lon. *E. coli* strain Origami B(DE3)pLysS and Rosetta-gami B(DE3)pLysS are deficient in trxB, gor, ompT and lon gene products. These mutations may be used in combination with any other host cells variations described above.

Also described in PCT/US2006/004413 is the use of a cleavage site engineered between thioredoxin and the disintegrin to enable isolation of the disintegrin from the fusion protein following expression. Any number of well known cleavage sites may be used for this purpose. A suitable protease cleavage site is the TEV protease cleavage site, which comprises the amino acid sequence ENLYFQG/S (three letter code: Glu-Asn-Leu-Tyr-Phe-Gln-Gly/Ser) (SEQ ID NO: 7). The TEV site may be engineered just upstream of the N-terminus of the disulfide containing disintegrin. A chemical cleavage site also may be used for this purpose. For example, a DP (Asp-Pro) dipeptide sequence can be engineered in a similar location to that of the TEV site in the fusion protein. Formic acid hydrolysis can then be used to cleave the protein at the DP site. The cleavage site is preferably placed between the thioredoxin and the disintegrin (e.g., downstream of the thioredoxin sequence and upstream of the N-terminal end of the disintegrin) in order to obtain the disintegrin free from thioredoxin.

Recombinantly expressed disintegrin may include functionally useful sequences that are taken or modeled from other proteins of the same structural class. These functional sequences, non-native to the disintegrin, may be located at either terminus of the disintegrin or within the distintegrin as dictated by the effect of the addition on the biological function of the disintegrin. Such functional sequences include the amino acid residues located downstream from the most C-terminal Cys residue in mono- or dimeric disintegrin primary sequences. For example, a biologically active disintegrin domain may include sequence at its C-terminus that directs binding to a particular type of integrin. For example, the CN full length disintegrin precursor or its disintegrin domain may be expressed with the C-terminal extension, HKGPAT (SEQ ID NO: 47) (three letter code: His-Lys-Gly-Pro-Ala-Thr), which represents the C-terminal amino acid sequence of echistatin, a disintegrin which is monomeric in its native state. The addition of the HKGPAT (SEQ ID NO: 47) at the C-terminus of the CN monomer can be used to increase the affinity of the expressed recombinant CN disintegrin domain for α5β1 integrin. This C-terminal fusion also can facilitate the proper folding of nascent recombinant CN disintegrin domain in the C-terminal half of the molecule where the integrin-binding loop key structural element resides.

Recombinantly expressed monomeric disintegrin or monomeric disintegrin domain may comprise a C-terminal sequence non-native to the disintegrin or disintegrin domain, such as the C-terminal sequence encoding a functional integrin-binding loop. In one embodiment, integrin binding loop is selected from any loops that bind to integrin αIbβ3, αvβ3, αvβ5, α5β1. In another embodiment, the integrin binding loop C-terminal sequence comprises HKGPAT (SEO ID NO: 47). In a further embodiment, the integrin binding loop is stabilized by at least one intramolecular disulfide bridge. In yet another embodiment, the monomeric disintegrin or monomeric disintegrin domain is from contortrostatin.

Pharmaceutical compositions containing homodimeric and monomeric disintegrins should comprise at a minimum an amount of protein effective to achieve the desired effect (i.e., inhibit cancer growth or prevent or inhibit cancer metastasis) and a suitable carrier or excipient. Generally, in these compositions, homodimeric and monomeric disintegrins are present in an amount sufficient to provide about 0.01 mg/kg to about 50 mg/kg per day, preferably about 0.1 mg/kg to about 5.0 mg/kg per day, and most preferably about 0.1 mg/kg to about 0.5 mg/kg per day.

Homodimeric and monomeric disintegrins may be administered by a variety of heretofore known means suitable for delivery thereof into the blood stream in substantial amounts. Intravenous administration of homodimeric and monomeric disintegrins in a suitable liquid vehicle or excipient is presently contemplated as the preferred route of administration. Homodimeric and monomeric disintegrins are soluble in water, and may therefore be effectively administered in a suitable aqueous solution (e.g., phosphate buffered saline). Alternatively, homodimeric and monomeric disintegrins may be administered orally (in the form of tablets or capsules formulated with a suitable binder or excipient material, or in the form of aqueous or oily suspensions, solutions, emulsions, syrups or elixirs) or as a parenteral suspension. As is well known in the art, adjuvants or excipients such as local anesthetics, preservatives, buffering agents, lubricants, wetting agents, colorants, flavorings, fillers and diluents may suitably be included in any of these formulations.

Preparation of Microtubule Stabilizing Agents

Microtubule stabilizing agents are combined with a disintegrin in the methods and compositions of the present invention. Taxanes, in particular paclitaxel, docetaxel and derivatives thereof, are preferred microtubule stabilizing agents for use in combination with a disintegrin in the methods and compositions of the invention. Taxanes have a common core structure (i.e., a taxoid core) shown below.

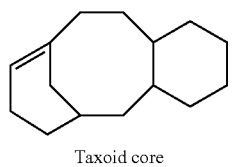

Taxoid core

The chemical structure of Taxol® and Taxotere® are shown below.

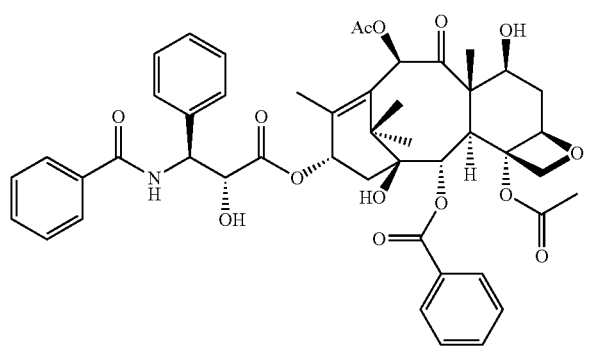

Taxol® (paclitaxel)

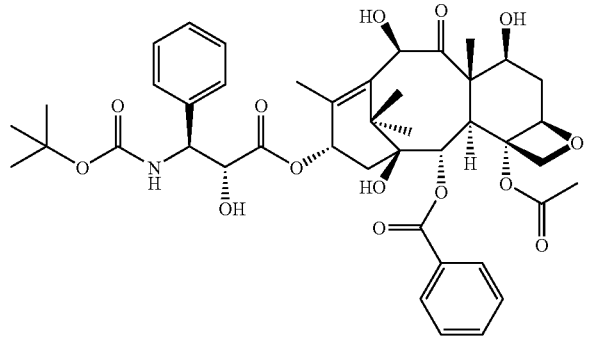

Taxotere® (docetaxel)

A number of non-natural taxanes have been prepared which have a taxane ring bearing modified side chains, which may include fatty acids. These modified taxanes or taxoid analogs inhibit cancer growth while having greater water solubility and stability than naturally occurring Taxol®. Exemplary derivatives of Taxol® are described in U.S. Pat. Nos. 6,638,742; 5,278,324; 5,272,171; 5,254,580; 5,250,683; 5,248,796; and 5,227,400; and US Pub. App. No. 2005/0148657; and the references cited therein, as well as those compounds disclosed in Villalva-Servín, et al., Can. J. Chem., 82:227-239 (2004); Shen, et al., Chem. Pharm. Bull., 53(7): 808-10 (2005); Ono, et al., Biol. Pharm. Bull., 27(3):345-51 (2004); Sampath, et al., Mol. Cancer Ther., 2(9):873-74 (2003); and Wolff, et al., Clin. Cancer Res., 9(10):3589-97 (2003).

In addition, non-taxane microtubule stabilizing agents, such as epothilones and derivatives thereof, also may be administered in combination with a disintegrin for the treatment of cancer in the methods and compositions of the present invention. Epothilones A and B (shown below), for example, have been found to exert microtubule stabilizing effects and cytotoxic activity against rapidly proliferating cells, such as tumor cells or other hyperproliferative cellular diseases, with results similar to those observed with Taxol®. Epothilones have a similar mechanism of action to taxanes despite the structural disimilarity. Epothilones, however, display some superior qualities to taxanes: namely water solubility, production in large quantities from bacteria fermentation, and retention of activity against multi-drug resistant cell lines and tumors. (See Giannakakou, et al., PNAS, 97(6): 2904-09 (2000) and references cited therein).

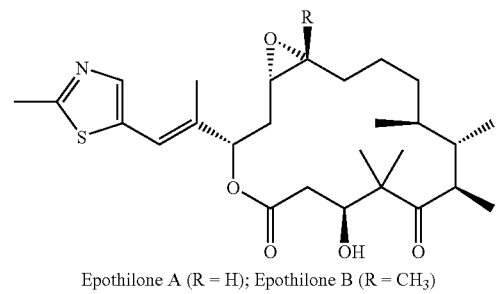

Epothilone A (R = H); Epothilone B (R = CH$_3$)

Epothilone derivatives have been previously administered in combination with therapeutic agents. For example, Mani, et al., describes administering the epothilone B derivative BMS-247550 in combination with capecitabine to breast cancer patients resistant to taxane therapy. See, e.g., Mani, et al., Clin. Cancer Res., 10:1289-98 (2004). BMS-247550 has been shown to have anti-tumor activity in paclitaxel-resistant tumor models. Id.

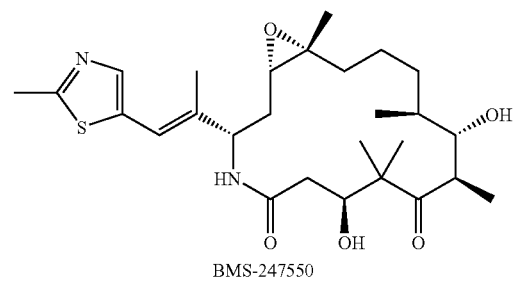

BMS-247550

Examples of epothilone compounds and derivatives contemplated for use herein are disclosed in U.S. Pat. Nos. 6,294, 374; 6,365,749; 6,380,394; 6,380,395; 6,387,927; 6,399,638; 6,441,186; 6,489,314; 6,498,257; 6,518,421; 6,531,497; 6,583,290; 6,589,968; 6,593,115; 6,596,875; 6,605,599; 6,605,726; 6,610,736; 6,624,310; 6,660,758; 6,670,384; 6,686,380; 6,689,802; 6,719,540; 6,727,276; 6,730,803; 6,780,620; 6,800,653; 6,831,090; 6,858,411; 6,867,333; 6,893,859; 6,900,331; 6,906,188; 6,921,650; 6,930,102; 6,930,187; 6,958,401; 6,982,276; 6,982,280; 6,998,256; and 7,008,936; and U.S. Pub. App. Nos. 20020042109; 20020045609; 20020062030; 20020143038; 20020156110; 20020165257; 20020165258; 20020169190; 20020188014; 20020193361; 20030004338; 20030023082; 20030045711; 20030060623; 20030073677; 20030087888; 20030144523; 20030144533; 20030149281; 20030176473; 20030176710; 20030186965; 20030187039; 20030187273; 20030191089; 20030203938; 20030219877; 20030220295; 20030220503; 20040014978; 20040023345; 20040024032; 20040030147; 20040038324; 20040039026; 20040049051; 20040053978; 20040058969; 20040072870; 20040072882; 20040082651; 20040092478; 20040127432; 20040132146; 20040132754; 20040157897; 20040176429; 20040214871; 20040253697; 20040259922; 20050038086; 20050042275; 20050113429; 20050159461; 20050187270; 20050192440; 20050267306; 20050282873; 20060013836; 20060014796; 20060040990; 20060046997; and 20060063815.

Other non-taxane microtubule stabilizing agents contemplated for use herein include taccalonolides and analogues thereof (see, e.g., U.S. Pat. No. 6,878,699 and U.S. Pub. App. No. 2002/0094991 and 2004/0022869); dictyostatin and analogues thereof (see, e.g., Madiraju et al., Biochem. 44(45) 15053-63 (2005)); laulimalide and analogues thereof (see Mooberry et al., PNAS 101(23) 8803-08 (2004)); and discodermolides and analogues thereof (see Kowalski et al., Mol. Pharm. 52(4) 613-22 (1997)).

A composition comprising a combination of a disintegrin or fragment thereof and a microtubule stabilizing agent can be administered as a pharmaceutical composition wherein the composition is formulated with a pharmaceutically acceptable carrier as is well known in the art. Techniques for formulation and administration may be found, for example, in "Remington's Pharmaceutical Sciences," (18th ed., Mack Publishing Co., Easton, Pa., 1990). Accordingly, the invention compounds and combination of compounds may be used in the manufacture of a medicament. It is understood that a pharmaceutically acceptable carrier, or a pharmaceutical composition, or any substance suitable for administration to a mammal should be manufactured and stored in accordance with standards of local regulations. For example, many governments have guidelines or rules that regulate various aspects of the manufacture and handling of compositions which are for administration into mammals and/or humans such as sanitation, process validation, equipment and document traceability, and personnel qualification. Preferably, a pharmaceutical composition or a pharmaceutically acceptable carrier is suitable for administration to a human and pharmaceutically complies with GMP (Good Manufacturing Practices) regulations set forth by the United States Food and Drug Administration for such a purpose.

A combination of a disintegrin and a microtubule stabilizing agent may be formulated as solutions or lyophilized powders for parenteral administration. Powders may be reconstituted by addition of a suitable diluent or other pharmaceutically acceptable carrier prior to use. Liquid formulations may be buffered, isotonic, aqueous solutions. Powders also may be sprayed in dry form. Examples of suitable diluents are normal isotonic saline solution, standard 5% dextrose in water, or buffered sodium or ammonium acetate solution. Such formulations are especially suitable for parenteral administration, but may also be used for oral administration or contained in a metered dose inhaler or nebulizer for insufflation. It may be desirable to add excipients such as polyvinylpyrrolidone, gelatin, hydroxy cellulose, acacia, polyethylene glycol, mannitol, sodium chloride, sodium citrate, and the like.

Alternately, a combination of a disintegrin and a microtubule stabilizing agent may be prepared for oral administration. Pharmaceutically acceptable solid or liquid carriers may be added to enhance or stabilize the composition, or to facilitate preparation of the vectors. Solid carriers include starch, lactose, calcium sulfate dihydrate, terra alba, magnesium stearate or stearic acid, talc, pectin, acacia, agar or gelatin. Liquid carriers include syrup, peanut oil, olive oil, saline and water. The carrier may also include a sustained release material such as glyceryl monostearate or glyceryl distearate, alone or with a wax. The amount of solid carrier varies but, preferably, will be between about 20 mg to about 1 g per dosage unit. When a liquid carrier is used, the preparation may be in the form of a syrup, elixir, emulsion, or an aqueous or non-aqueous suspension.

A combination of a disintegrin and a microtubule stabilizing agent may be formulated to include other medically useful drugs or biological agents and/or may be administered in conjunction with the administration of other drugs or biological agents useful for the disease or condition that the invention compounds are directed.

The dosage to be administered depends to a large extent on the condition and size of the subject being treated as well as the frequency of treatment and the route of administration. Regimens for continuing therapy, including dose and frequency may be guided by the initial response and clinical judgment. For general purposes, the small molecule microtubule stabilizing agent could be administered at about 60-75 mg/m$^2$ every 3 weeks while the disintegrin dose could be from 0.1 mg/kg to 1 mg/kg for each administration.

As such, the invention provides a pharmaceutical product, comprising a combination of a disintegrin and a microtubule stabilizing agent, in solution in a physiologically acceptable injectable carrier and suitable for introduction into an individual, a container enclosing the solution, and a notice associated with the container in form prescribed by a governmental agency regulating the manufacture, use, or sale of pharmaceuticals, which notice is reflective of approval by the agency of manufacture, use, or sale of the solution of the combination (or separate individual components) for human administration.

Disintegrin and/or microtubule stabilizing agents may be delivered by way of liposomes, which may incorporate one or both of these compounds. Liposomal delivery is well known in the art and has been described for delivery of both disintegrins and microtubule stabilizing agents. For example, Swenson et al. Cancer Ther. 2004, 3(4):499-511 describes use of intravenous delivery of contortrostatin in liposomes for therapy of breast cancer. See also, Fujii, Chang et al. Biochemistry 1997, 36(16):4959-68.

Another embodiment is to administer an expression vector encoding the disintegrin to obtain the disintegrin by recombinant expression in the individual with cancer. An expression vector encoding the disintegrin can be formulated to facilitate transfection delivery to the interior of a cell, and/or to a desired location within a cell. Many such transfection facilitating materials are commercially available, for example Lipofectin, Lipofectamine, Lipofectamine 2000, Optifect, SuperFect. Examples of transfection facilitating materials include, but are not limited to lipids, preferably cationic lipids; inorganic materials such as calcium phosphate, and metal (e.g., gold or tungsten) particles (e.g., "powder" type delivery solutions); peptides, including cationic peptides, targeting peptides for selective delivery to certain cells or intracellular organelles such as the nucleus or nucleolus, and amphipathic peptides, i.e., helix forming or pore forming peptides; basic proteins, such as histones; asialoproteins; viral proteins (e.g., Sendai virus coat protein); pore-forming proteins; and polymers, including dendrimers, star-polymers, "homogenous" poly-amino acids (e.g., poly-lysine, poly-arginine), "heterogeneous" poly-amino acids (e.g., mixtures of lysine & glycine), co-polymers, polyvinylpyrrolidinone (PVP), and polyethylene glycol (PEG). Furthermore, those auxiliary agents of the invention which facilitate and enhance the entry of a polynucleotide into vertebrate cells in vivo, may also be considered "transfection facilitating materials."

Lipofection facilitated transfection is well known in the art as described, for example, in U.S. Pat. Nos. 6,034,072, 6,040,295 and 6,710,035. Certain embodiments may include lipids as a transfection facilitating material, including cationic lipids (e.g., DOTMA, DMRIE, DOSPA, DC-Chol, GAP-DL-RIE), basic lipids (e.g., steryl amine), neutral lipids (e.g., cholesterol), anionic lipids (e.g., phosphatidyl serine), and zwitterionic lipids (e.g., DOPE, DOPC). Preferably, the cationic lipid is mixed with one or more co-lipids. For purposes of definition, the term "co-lipid" refers to any hydrophobic material which may be combined with the cationic lipid component and includes amphipathic lipids, such as phospholipids, and neutral lipids, such as cholesterol. Cationic lipids and co-lipids may be mixed or combined in a number of ways to produce a variety of non-covalently bonded macroscopic structures, including, for example, liposomes, multilamellar vesicles, unilamellar vesicles, micelles, and simple films.

Viral vectors suitable for delivery in vivo and expression of a disintegrin are well known and include adenoviral vectors, adeno-associated viral vectors, retroviral vectors, herpes simplex viral vectors, and the like. Viral vectors are preferably made replication defective in normal cells. See U.S. Pat. Nos. 6,669,942; 6,566,128; 6,794,188; 6,110,744; and 6,133,029. Suitable adenoviral vectors include those capable of replicating and being packaged when any deficient essential genes are provided in trans. A suitable adenoviral vector desirably contains at least a portion of each terminal repeat required to support the replication of the viral DNA, preferably at least about 90% of the full ITR sequence, and the DNA required to encapsidate the genome into a viral capsid. Many suitable adenoviral vectors have been described in the art. See U.S. Pat. Nos. 6,440,944 and 6,040,174 (replication defective E1 deleted vectors and specialized packaging cell lines). A preferred adenoviral expression vector is one that is replication defective in normal cells.

Adeno-associated viruses represent a class of small, single-stranded DNA viruses that can insert their genetic material at a specific site on chromosome 19. The preparation and use of adeno-associated viral vectors for gene delivery is described in U.S. Pat. No. 5,658,785.

Non-viral vectors for gene delivery comprise various types of expression vectors (e.g., plasmids) which are combined with lipids, proteins and other molecules (or combinations of thereof) in order to protect the DNA of the vector during delivery. Fusigenic non-viral particles can be constructed by combining viral fusion proteins with expression vectors as described. Kaneda, Curr. Drug Targets (2003) 4(8):599-602. Reconstituted HVJ (hemagglutinating virus of Japan; Sendai virus)-liposomes can be used to deliver expression vectors or the vectors may be incorporated directly into inactivated HVJ particles without liposomes. See Kaneda, Curr Drug Targets (2003) 4(8):599-602. DMRIE/DOPE lipid mixture are useful a vehicle for non-viral expression vectors. See U.S. Pat. No. 6,147,055. Polycation-DNA complexes also may be used as a non-viral gene delivery vehicle. See Thomas et al., Appl Microbiol Biotechnol (2003) 62(1):27-34.

Various examples describing genetic delivery and expression of a disintegrin and achieving therapeutic cancer effects have been reported. See, e.g., Soo In Kim et al., Cancer Research 63: 6458-62 (2003).

The versatility of the invention is illustrated by the following Examples which illustrate preferred embodiments of the invention and are not limiting of the claims or specification in any way.

EXAMPLES

Example 1

Expression of Contortrostatin in Origami B strain of *E. coli*

The sequence HKGPAT (SEQ ID NO: 47), which represents the C-terminal amino acid sequence of the monomeric disintegrin, echistatin, was included at the C-terminal end of the CN disintegrin domain sequence. This construct is a chimera that combines by the means of genetic engineering the sequences of two snake venom disintegrins with different originis: echistatin (a viperid disintegrin) and contortrostatin (a crotalid disintegrin). For this reason, this disintegrin construct that carries a C-terminal graft is referred to as "Vicrostatin" or "VN." CN disintegrin domain without the HKGPAT (SEQ ID NO: 47) sequence is referred to as "rCN" or "rCN construct." The amino acid sequence of vicrostatin is shown below as SEQ ID NO: 8

(SEQ ID NO: 8)
GDAPANPCCDAATCKLTTGSQCADGLCCDQCKFMKEGTVCRRARGDDLDD

YCNGISAGCPRNPHKGPAT.

The sequence of VN results from its expression as a fusion to thioredoxin and post expression processing as described below.

Contortrostatin wild-type disintegrin domain or the disintegrin domain with echistatin C-terminal graft was directionally cloned by PCR into the pET32a vector (Novagen, Inc.), downstream of the thioredoxin sequence. The set of restriction enzymes used for cloning was: BglII/NcoI. The oligonucleotide primers employed for cloning were as follows:

CNfor1—forward primer for rCN (disintegrin domain) and VN (disintegrin domain) introducing BglII restriction site (SEQ ID NO: 9)
5'GTTCCAGATCTCGAGAATCTTTACTTCCAAGGAGACGCTCCTGCAAAT

CCGTGCTGCGATGCTGCA3'

CNback1—reverse primer for rCN (disintegrin domain) introducing the NcoI restriction site (SEQ ID NO: 10)
5'GTTATTCGCCATGGCTTAGGCATGGAAGGGATTTCTGGGACAGCCAGC

AGA3'

CNback2—reverse primer for VN (disintegrin domain) introduction the NcoI restriction site (SEQ ID NO: 11)
5'GTTATTCGCCATGGCTTAAGTAGCTGGACCCTTGTGGGATTTCTGGG

ACAGCCAGCAGATATGCC3'

The forward primer introduces a unique TEV protease cleavage site, which makes possible the removal of the thioredoxin fusion partner after purification of the fusion protein by Ni-column chromatography. The TEV protease recognizes with high specificity the canonical ENLYFQG (SEQ ID NO: 54) amino acid sequence engineered between recombinant CN and the thioredoxin fusion partner in this construct and following cleavage leaves a glycine at the N-terminus of rCN and VN. The reverse primer grafts the HKGPAT (SEQ ID NO: 47) segment to the C-terminus of the fusion protein. Thus, two recombinant fusion proteins, designated Trx-rCN and Trx-VN, were generated using the above described cloning strategy.

The initial cloning was carried out in the DH5α strain, which is recA⁻ endA⁻ and has high transformation efficiency and good plasmid yield. After validating the cloning by sequencing the constructs retrieved from DH5α transformants, the vector was used to transform the expression host, Origami B(DE3)pLysS, for expression optimization.

The Origami B/pET32a system produced up to 20 mg/L of recombinant CN (both Trx-rCN and Trx-VN constructs) without optimization. A single colony of transformed Origami B cells was used to inoculate a primary culture containing 10 mL LB broth with carbenicillin (100 μg/mL), tetracycline (12.5 μg/mL), kanamycin (15 μg/mL) and chloramphenicol (34 μg/mL). The culture was grown overnight to high turbidity and was used to inoculate 1 L of fresh LB broth with all 4 antibiotics. The first culture was used to inoculate a larger volume of LB broth plus antibiotics which was grown at 37° C. with shaking at 250 rpm to an $OD_{600}$ of 1-2. At this point, 1 mM IPTG was added and the cells further grown for another 3-5 hours at 37° C. with shaking at 250 rpm.

The cells were harvested and resuspended in 5 mL of cold 20 mM Tris-HCl, pH 7.5, and lysed by sonication. The insoluble cellular debris was removed by centrifugation at 40,000×g and the total soluble protein fraction collected. The total soluble protein fractions retrieved from cell lysates and analyzed by SDS-PAGE showed that the fusion proteins (Trx-rCN and Trx-VN) were the prevalent species in this cell fraction.

The fusion proteins in the total soluble protein fractions were subjected to proteolysis by recombinant TEV protease following the manufacturer's protocol (Invitrogen, Carlsbad, Calif.) so as to cleave rCN or VN from its fusion partner, thioredoxin. Following TEV protease treatment (monitored by SDS-PAGE), the protein lysates were sterilized by passage through a 0.22 μm filter and further passed through a 30 kDa molecular cut-off filter (Millipore, Bedford, Mass.). The recombinant disintegrin species (rCN or VN) contained in the filtrate were further recovered by reverse phase HPLC purification. Alternatively, the fusion proteins containing a His-tag sequence were initially purified by Ni-chelation affinity chromatography using a commercially available His•Bind resin kit (Novagen, Madison, Wis.). After buffer exchange (removal of imidazole excess), the fusion proteins were subjected to overnight proteolysis at room temperature using TEV protease in the presence of a very small amount of DTT or GSH/GSSG to keep the TEV protease (a cysteine-protease) in a reduced (active) state. When proteolysis was complete (assessed by SDS-PAGE), the recombinant CN species (rCN or VN) were recovered by reverse phase HPLC purification.

C18-Reverse Phase HPLC was employed to purify recombinant CN constructs following TEV cleavage of the fusion protein. The HPLC column conditions used for rCN and VN were the same as for native CN. HPLC was conducted using a Vydac C18 column (218TP54, Temecula, Calif.) in a solution of 0.1% TFA in water. A ten-minute rinse (at 1 ml/ml) of the column with the loading solution was followed by a linear gradient (0-100%) elution over 50 minutes with a mobile phase containing 80% acetonitrile in 0.1% TFA. Under these conditions, native CN and both forms of recombinant CN elute at 41% acetonitrile. The eluted material analyzed by reducing SDS-PAGE showed that VN as a single band with a molecular weight of ~8 kDa, slightly larger than native CN, which agrees with the primary structure containing five additional amino acids. The recovered rCN was almost identical in size to native CN.

HPLC purified rCN and VN were recognized by a polyclonal antisera raised against native CN in both ELISA and Western blotting assays (data not shown).

Example 2

Biological Activity of Recombinant Contortrostatin Constructs

A. In Vitro Functional Assays

The recombinant CN products were evaluated for biological activity by a platelet aggregation inhibition assay. According to this assay, CN binding to GPIIb/IIIa (integrin αIIbβ3) in an RGD dependent manner inhibits ADP induced platelet aggregation (Trikha, Rote, et al. 1994). In this assay, potential inhibitors are added to fresh platelet-rich plasma, and after minute, ADP is added to a final concentration of 1 μM to induce aggregation. If inhibitor is present, functional aggregation will not occur. The $IC_{50}$ is defined as the concentration at which 50% of the activity is inhibited, and is used as a measure of the potency of an inhibitor.

It was shown that VN exhibited an $IC_{50}$ of 59 nM in the platelet inhibition assay, which is almost identical to that observed for native CN. The rCN conformer however did not inhibit platelet aggregation, even at low μM concentrations which are effective for small, synthetic RGD peptides. Furthermore, the chimeric recombinant disintegrin VN showed similar results in several other in vitro integrin-based functional assays: inhibition of MDA-MB-435 carcinoma cell adhesion to immobilized fibronectin (Fn) and vitronectin (Vn), or inhibition of MDA-MB-435 cell invasion through an artificial basement membrane (Matrigel) in a modified Boyden chamber. For the cell adhesion assay, the pretreatment MDA-MB-435 breast carcinoma cells with various concentrations (0-1000 nM) of either native CN or VN for 30 min inhibited adhesion of MDA-MB-435 cells (100 μl of cells, 105 cells/ml) to either immobilized fibronectin (Fn) or vitronectin (Vn). Pretreated cells were allowed to adhere for 1 hr at 25° C., and after non-adherent cells were washed away, the number of adherent cells for each condition was estimated using the MTS cell viability assay. In the cell invasion assay, an invasion chamber consisting of cell culture inserts that fit into 24-well tissue culture plate has been utilized. The inserts contain an 8 μm-pore size polycarbonate membrane, over which a thin layer of ECMatrix™ was applied. The ECMatrix™ serves as an in vitro reconstituted basement membrane and is a solid gel of ECM proteins prepared from the Engelbreth Holm-Swarm (EHS) mouse tumor. The ECM layer occludes the membranes pores, blocking non-invasive cells to migrate through. The cells were incubated in the presence of various concentrations (10, 100, 1000 nM) of either native CN or Vicrostatin for 30 min at 25° C. and then allowed to migrate in the Boyden chamber for 8 hrs. At the 8 hr time point the cells that invaded through the pores into the lower chamber were measured. The numbers of invaded cells for each condition were approximated by quantitating the retrieved labeled DNA using a fluorescent plate reader. The results were calculated in % invasion, where the untreated control was considered as 100% invasion. In all these in vitro functional assays, only Vicrostatin (VN) showed the same potency and exhibited and $IC_{50}$ almost identical to that of native CN. In all in vitro functional assays tested, rCN construct was inactive in the nanomolar range.

B. Preparation of Recombinant Disintegrin Containing Liposomes

Endotoxin-free VN containing liposomes (referred to as LVN) and endotoxin-free native CN containing liposomes (referred to as LCN) were prepared utilizing a probe sonication previously described (Fujii, Chang et al. 1997). Briefly, the lipids (disteroylphosphatidylcholine, cholesterol and polyethylene glycol derivatized lipid) were dissolved in a chloroform/methanol solution. Thin lipid films were created by pipetting aliquots of the lipid solution into round bottom glass tubes followed by solvent evaporation at 65° C. under a stream of nitrogen gas. The films were placed under vacuum for at least 24 hours to remove residual organic solvent. Liposomes formed following hydration of the lipid films with native CN or VN dissolved in 10 mM sodium phosphate, 9% sucrose, pH 7.2. The mixture was incubated at 65° C. for 5-10 minutes. Hydration was followed by probe sonication until the suspension was translucent. The resultant suspension contained liposomes entrapping CN/VN and unencapsulated CN/VN. The unencapsulated fractions were removed by ultrafiltration. Following clean-up, the suspension was sterilized by passage through a 0.22 µm filter.

The concentration of liposome entrapped CN/VN was determined by disruption of the liposomes with chloroform/methanol/water (10:40:50) followed by centrifugation at 14,000×g. The supernatant was analyzed for CN/VN concentration using BCA protein assay (Smith et al., Anal. Biochem. 150(1): 76-85 (1985)). The encapsulation efficiency was assessed by BCA protein determination following disruption of the LrCN with a solution of $H_2O$ methanol: chloroform.

It was observed that 72% of the recombinant protein VN in the encapsulation solution was entrapped within the liposomes, as compared to 80% with native CN. LVN showed identical stability and size distribution (average particle size 140 nm) as encapsulated native CN.

C. Tumor Therapy Using Recombinant Disintegrin-Containing Liposomes

Biological activity of liposome encapsulated CN was evaluated as previously described (Swenson et al. (2004)). Briefly, three groups of five nude mice had MDA-MB-435 human mammary carcinoma cells implanted in the mammary fat pad. Two weeks following implantation, small tumors were palpable and treatment was commenced. Animals were treated with LCN or LVN (105 µg, twice weekly, i.v. administration); a PBS treated control was included. A significant inhibitory effect on tumor growth by LVN was observed. The functional activity of VN was indicated by its in vivo cancer therapeutic effect, which was found to be similar to native CN.

D. Anti-Angiogenic Activity of Recombinant Disintegrin-Containing Liposomes

Previous in vivo studies with native CN and encapsulated native CN (LCN) demonstrated a dramatic inhibitory effect on angiogenesis in growing tumors (Zhou, Nakada et al. (1999); Zhou, Sherwin et al. (2000); Markland et al. (2001); Golubkov et al., Angiogenesis 6(3): 213-24 (2003); Swenson et al. (2004)). Consequently, the effect of LVN on tumor angiogenesis in the MDA-MB-435 breast cancer model was examined by histochemical identification of blood vessels with anti-CD31 (anti-PECAM-1) monoclonal antibody. CD31 has been reported to be highly expressed in the angiogenic vasculature with approximately one million copies reported on the surface of endothelial cells (Newman, Ann. N.Y. Acad. Sci. 714: 165-74 (1994)). CD31 also has been reported to be involved with the initial formation and stabilization of cell-cell contacts at lateral junctions of endothelial cells, the maintenance of the vascular permeability barrier, the regulation of cell migration, and the formation of new blood vessels during angiogenesis (Newman et al., Science 247(4947): 1219-22 (1990); Ferrero et al., FEBS Lett. 374(3): 323-26 (1995); DeLisser et al., Am. J. Pathol. 151(3): 671-77 (1997)). These combined properties of CD31 make it an optimal reporter molecule for determinations of angiogenic growth.

Briefly, tumors from treated and untreated mice from the LCN/LVN efficacy studies in the MDA-MB-435 animal tumor model were fixed in 4% normal buffered formalin and embedded in paraffin blocks as previously described (Shi et al. J. Histochem. Cytochem 39(6): 741-48 (1991)). The paraffin blocks were cut into 5 µm sections and placed on glass slides. Tissue sections underwent deparaffinazation, rehydration, and antigen retrieval as described previously (Pileri, Roncador et al., J. Pathol. 183(1): 116-23 (1997)). Endogenous peroxidase activity was blocked by exposure of the sections to 3% $H_2O_2$. Specimens were blocked with normal goat serum (1:20) for 30 minutes, followed by incubation with the primary antibody for 1 hour. Rabbit monoclonal antibody to CD31 (Sigma, St. Louis, Mo.) was used as a primary antibody to detect small vessels. The secondary (detection) goat anti-rabbit antibody conjugated with peroxidase (Zymed, San Francisco, Calif.) was then applied to the samples and incubated for 10 minutes at room temperature followed by removal of unbound antibody by multiple washes with PBS. Detection of the secondary antibody using 3,3'-diaminobenzidine (DAB) as the chromogen, was performed following the manufacturers instructions (Zymed HistoMouse Max). Slides were counterstained with hematoxylin. Quantitation of the stained vessels was performed using "hot spot" analysis (Gasparini et al., Int. J. Cancer 55(5): 739-44 (1993)), with "hot spots" being defined as areas of high vessel density (Weidner et al., J. Natl. Cancer Inst. 84(24): 1875-87 (1992); Swenson et al. (2004)). Areas showing positive staining (100× magnification) were quantitated in terms of pixels within a given hot spot using SimplePCI advanced imaging software (C-Imaging Systems, Cranberry Township, Pa.).

Vessel detection by CD31 in MDA-MB-435 tumor sections indicated differences in positive staining in each of the treatment groups: PBS, intravenous liposomal encapsulated native CN (LCN) and intravenous liposomal encapsulated VN (referred to as LVN). In both the LCN, and LVN treated tumors, there is a statistically significant (p<0.0005) reduction of microvascular density, which corresponds to a 90% reduction in angiogenesis in the LCN group and 92% reduction in the LVN group. The reduction in angiogenesis, as observed by CD31 immunostaining in all treatment groups in the MDA-MB-435 breast cancer xenograft model indicates that LVN is an effective inhibitor of angiogenesis.

E. Structural Analysis of Recombinant Disintegrin

The structure of native CN and VN was evaluated by mass spectrometry. MALDI-TOF mass spectrometry was performed using a matrix of α-cyano-4-hydroxycinnamic acid. Native CN was observed as a dimer while VN was observed as a monomeric peak with Mr of 7143.41.

Electron spray ionization mass spectrometry was also used to evaluate native CN and VN. A large peak of 13507.0, for CN representing the dimer was observed, and two smaller peaks, probably CN, representing a single amino acid cleavage fragment. A single peak of 7146.0, for VN was observed confirming that it is a monomer.

Mass spectrometry data showed that VN is a monomeric structure unlike the dimer form of native CN. Because the biological activities measured for CN as described above reside in the C-terminal portion of the molecule, this indicates that VN folded correctly at least in the C-terminal part of the molecule, making the correct disulfide bridge combinations and preserving the integrin binding loop that exists in the native conformer. However, the failure to obtain the native dimer configuration indicates that the N-terminal portion of VN folded in a different manner than native CN, which compromised the ability of the N-terminal cysteines of VN to participate in intermolecular disulfide bond formation. This was confirmed by the detection of at least one free thiol in VN. The first cysteine residue (Cys-7) which pairs in the native state with the seventh cysteine (Cys-30) in CN are the furthest apart of the cysteines that bridge in CN. Difficulty inherent in bridging the C7 and C30 cysteines in CN is a possible explanation for the failure of VN to form dimers.

Example 3

Optimizing Codon Usage

A potential issue with Origami E. coli strain (FA113) is its lack of codon usage optimization. In many organisms, not all of the 61 tRNA species are used equally. The so-called major codons are those that occur in highly expressed genes, whereas the minor or rare codons tend to be in genes expressed at lower levels; which of the 61 codons are the rare ones depends strongly on the organism.

Eukaryotic proteins tend to translate inefficiently in E. coli because of mismatched codon use that hampers protein production in heterologous expression systems (Makrides, Microbiol. Rev. 60(3): 512-38 (1996)). The codon usage per organism can be found in codon usage databases well known in the art and available online.

The following overlapping oligonucleotide primers were generated and used to replace the CGG and ACA codons in the wild type CN gene.

CNCGGfor—CN disintegrin domain forward primer that replaces CGG and the eleventh ACA codons:

(SEQ ID NO: 12)
5'ACCGTATGCCGTAGAGCAAGGGGTGATGACCTGGATGATTAC3'

CNCGGback—CN disintegrin domain reverse primer that replaces CGG and the eleventh ACA codons:

(SEQ ID NO: 13)
5'TGCTCTACGGCATACGGTTCCTTCTTTCATAAATTTGCACTG3'

CNACAfor—CN disintegrin domain forward primer that replaces the eight, ninth and tenth ACA codons:

(SEQ ID NO: 14)
5'TGCGATGCTGCAACCTGTAAACTGACCACCGGGTCACAGTGTGCAGAT3'

CNACAback—CN disintegrin domain reverse primer that replaces the eight, ninth and tenth ACA codons:

(SEQ ID NO: 15)
5'CAGTTTACAGGTTGCAGCATCGCAGCACGGATTTGC3'

CNMACA12for—CN metalloprotease domain forward primer that replaces the first two ACA codons:

(SEQ ID NO: 16)
5'TCTGATGGCAGAAAAATTACCACCAACCCTCCGGTTGAG3'

CNMACA12back—CN metalloprotease domain reverse primer that replaces the first two ACA codons:

5'AATTTTTCTGCCATCAGAGGAATAATG3' (SEQ ID NO: 17)

CNMACA45for—CN metalloprotease domain forward primer that replaces the fourth and fifth ACA codons:

(SEQ ID NO: 18)
5'CATAGTGCAATAAATCTTTGGGTTGCAGTTACTATGGCCCATGAG3'

CNMACA45back—CN metalloprotease domain reverse primer that replaces the fourth and fifth ACA codons:

(SEQ ID NO: 19)
5'ATTTATTGCACTATGATCCTGAACAATTCCGGTAGAAAGCTTCGG3'

Example 4

Engineered Hosts System

An engineered Rosetta-gami B host with disulfide isomerase activity in the cytoplasm and including auto-regenerating capabilities for its oxido-reductive enzymatic equipment in the same compartment may be used for recombinant CN production in bacteria. The host can be engineered to concomitantly overexpress in its cytoplasm the disulfide containing eukaryotic protein fused to thioredoxin along with ΔssDsbC and ΔssDsbDα. This goal can be achieved using a pair of vectors that can coexist together in the same system. The minimum features of this vector set are: the presence of a strong promoter-like T7lac, that can be used for all three proteins simultaneously, as well as the presence of convenient multiple restriction sites in different MCSs (multiple cloning sites) incorporated in the vectors. Two Novagen vectors (pET32a and pCDFDuet-1) that are compatible with each other by having different replicons, and also compatible with Rosetta-gami expression host, have the aforementioned characteristics and may be used in the system described herein. By employing these two vectors, the scenario of using an integrated system, in which the expression of all three proteins would be simultaneously controlled by a single strong promoter T7lac, is achieved.

Several wild-type and active site mutated thioredoxin-CN genetic constructs were prepared which express a fusion protein containing thioredoxin at the N-terminus and disintegrin domain (CN), or with the disintegrin domain including echistatin C-terminal graft (VN), or with larger eukaryotic proteins consisting of proprotein, metalloproteinase and disintegrin domains of CN with or without the echistatin C-terminal graft (designated rCN PMD and VN PMD). The broad term "TrxA-disintegrin construct" used below refers to the following constructs prepared as described herein: TrxA-rCN (thioredoxin A fused to CN disintegrin domain), TrxA-VN (thioredoxin A fused to CN disintegrin domain including echistatin C-terminal graft), TrxA-rCN PMD (thioredoxin A fused to a large protein consisting of CN proprotein, metalloproteinase and disintegrin domains), TrxA-VN PMD (thioredoxin A fused to a large protein consisting of CN proprotein, metalloproteinase and disintegrin domains with echistatin C-terminal graft), TrxA (CPYC (SEQ ID NO: 49))-rCN (an active site mutated thioredoxin A with the CPYC (SEQ ID NO: 49) motif fused to CN disintegrin domain), TrxA (CPYC (SEQ ID NO: 49))-VN (an active site mutated thioredoxin A including the CPYC (SEQ ID NO: 49) motif fused to CN disintegrin domain with echistatin C-terminal graft), TrxA (CPYC (SEQ ID NO: 49))-rCN PMD (an active site thioredoxin A including the CPYC (SEQ ID NO: 49) motif fused to a large protein consisting of CN proprotein, metalloproteinase and disintegrin domains), TrxA (CPYC (SEQ ID NO: 49))-VN PMD (an active site thioredoxin A including the CPYC (SEQ ID NO: 49) motif fused to a large protein consisting of CN proprotein, metalloproteinase, and disintegrin domains with echistatin C-terminal graft), TrxA (CGHC (SEQ ID NO: 50))-rCN (an active site mutated thioredoxin A including the CGHC (SEQ ID NO: 50) motif fused to CN disintegrin domain), TrxA (CGHC (SEQ ID NO: 50))-VN (an active site mutated thioredoxin A including the CGHC (SEQ ID NO:50) motif fused to CN disintegrin domain with echistatin C-terminal graft), TrxA (CGHC (SEQ ID NO: 50))-rCN PMD (an active site mutated thioredoxin A including the CGHC (SEQ ID NO: 50) motif fused to a large protein consisting of CN proprotein, metalloproteinase and disintegrin domains), and TrxA (CGHC (SEQ ID NO: 50))-VN PMD (an active site mutated thioredoxin A including the CGHC (SEQ ID NO: 50) motif fused to a large protein consisting of CN proprotein, metalloproteinase and disintegrin domains with echistatin C-terminal graft).

To increase the stability of some recombinant eukaryotic protein transcripts in the cytoplasm of the expression host, especially of those large transcripts containing the proprotein, metalloprotease and disintegrin domains (with or without echistatin C-terminal graft), some recombinant constructs were designed to include nucleotide sequences of various length that can normally be found in the 3' non-translatable regions of CN native mRNA, downstream of the stop codon signaling the end of translation found in the CN native transcript. Several disintegrin constructs were cloned with extra non-coding nucleotide regions modeled from CN native mRNA by using CN cDNA as a template (Zhou, Hu et al. 2000). Native CN cDNA is available in Francis S. Markland laboratory at USC.

The primers that were used to PCR clone downstream of TrxA nucleotide sequence, the CN disintegrin domain sequence with or without the echistatin C-terminal graft or the larger CN sequences consisting of proprotein, metalloprotease, and disintegrin domains with or without echistatin C-terminal graft into the pET32a vector were the following:

CNfor2—forward primer for CN disintegrin domain introducing the NcoI restriction site and the TEV protease cleavage site:

(SEQ ID NO: 20)
5'GTTCCCCATGGATGAGAATCTTTACTTCCAAGGAGACGCTCCTGCAAA

TCCGTGCTGCGATGCTGCA3'

CNfor3—forward primer for full-length CN introducing the NcoI restriction site and the TEV protease cleavage site:

(SEQ ID NO: 21)
5'GTTCCCCATGGATGAGAATCTTTACTTCCAAGGAATGATCCAGGTTCT

CTTGGTGACTCTATGCTTA3'

CNback3—reverse primer for CN constructs without echistatin C-terminal graft introducing the EcoRI restriction site:

(SEQ ID NO: 22)
5'GTTATTCGGAATTCTTAGGCATGGAAGGGATTTCTGGGACAGCCAGCA

GA3'

CNback4—reverse primer for CN constructs with echistatin C-terminal graft introducing the EcoRI restriction site:

(SEQ ID NO: 23)
5'GTTATTCGGAATTCTTAAGTAGCTGGACCCTTGTGGGGATTTCTGGGA

CAGCCAGCAGATATGCC3'

The reverse primers used to clone various disintegrin constructs including the non-translatable nucleotide sequences of CN native mRNA into the pET32a vector were the following:

CNback5—reverse primer for generating CN native transcripts introducing the EcoRI restriction site:

(SEQ ID NO: 24)
5'GTTATTCGGAATTCATATTACAGAATTTGGATACCATCTGGAAGCT

A3'

CNback6—reverse primer for generating CN native transcripts introducing the EcoRI restriction site:

(SEQ ID NO: 25)
5'GTTATTCGGAATTCGAATGAGAATAGTTTGTTTATTGACGGAAGCA

G3'

The oligonucleotide primers that were used to amplify the active-site thioredoxin mutants and clone them into pET32a vector replacing the wild type TrxA nucleotide sequence were the following:

Trxfor—Trx forward external primer introducing the XbaI restriction site and designed for inserting the 5' end of the active site mutants into pET32a vector:

5'CCCCTCTAGAAATAATTTTGTTTAACT3'    (SEQ ID NO: 26)

Trxback—Trx reverse external primer introducing the BglII restriction site and designed for inserting the 3' end of the active site mutants into pET32a vector:

5'TACCCAGATCTGGGCTGTCCATGTGCT3'    (SEQ ID NO: 27)

TrxGrxfor—Trx forward primer that mutates TrxA active site to a glutaredoxin-like one:

(SEQ ID NO: 28)
5'TTCTGGGCAGAGTGGTGCCCGTATTGCAAAATGATCGCCCCG3'

TrxGrxback—Trx reverse primer that mutates TrxA active site to a glutaredoxin-like one:

5'GCACCACTCTGCCCAGAAATC3'    (SEQ ID NO: 29)

TrxPDIfor—Trx forward primer that mutates TrxA active site to a PDI-like one:

(SEQ ID NO: 30)
5'TTCTGGGCAGAGTGGTGCGGTCATTGCAAAATGATCGCCCCG3'

TrxPDIback—Trx reverse primer that mutates TrxA active site to a PDI-like one:

5'GCACCACTCTGCCCAGAAATC3'    (SEQ ID NO: 31)

For DsbD cloning, the restriction sites employed were NcoI/EcoRI. This restriction enzyme pair was used because it removed the His tag-sequence from the pCDFDuet-1 vector first multiple cloning site, so ΔssDsbD α-domain would be expressed as a non-tagged molecule. For DsbC cloning the NdeI/XhoI restriction enzyme pair was used, so that ΔssDsbC protein would be expressed un-tagged.

Wild type DsbC gene carries an EcoRI restriction site. For this reason, the foldase sequences were cloned by PCR in a stepwise manner as following: the ΔssDsbD α-domain nucleotide sequence was inserted in one multiple cloning site of pCDFDuet-1 vector in the first cloning step, followed by ΔssDsbC nucleotide sequence, which was inserted in the other multiple cloning site of the vector in a second cloning step. The only His-tagged proteins expressed in the system described herein were the TrxA-disintegrin fusion constructs, so they can be easily separated from the other two co-over-expressed proteins by employing the Ni-column chromatography purification technique. All TrxA-disintegrin constructs included a TEV protease cleavage-site engineered just upstream of the disulfide containing recombinant protein (eukaryotic protein) nucleotide sequences. All purification steps of TrxA-disintegrin constructs were performed in the identical manner to those described in the section discussing the Origami system. However, some TrxA-disintegrin constructs also carried a formic acid cleavage site (Asp-Pro) instead of a TEV protease cleavage site, also engineered just upstream of the N-terminus of disulfide containing recombinant eukaryotic protein nucleotide sequences. Use of formic acid for hydrolysis reduces costs as compared with other protease cleavage systems such as the TEV proteolysis system.

The oligonucleotide primers that were used to clone various disintegrin constructs engineered to carry an Asp-Pro formic acid cleavage site just upstream of the N-terminus of various CN constructs (with or without multiple domains or echistatin C-terminal graft) into pET32a vector were the following:

CNfor4—forward primer for CN disintegrin domain introducing the NcoI restriction site and the Asp-Pro cleavage site:

(SEQ ID NO: 32)
5'GTTCCCCATGGATGACCCTGCAAATCCGTGCTGCGATGCTGCAACA3'

CNfor5—forward primer for full-length CN introducing the NcoI restriction site and the Asp-Pro cleavage site:

(SEQ ID NO: 33)
5'GTTCCCCATGGATGACCCTATGATCCAGGTTCTCTTGGTGACTCTATG
CTTA3'

The oligonucleotide primers that were used to PCR clone the ΔssDsbC, ΔssDsbD α-domain nucleotide sequences as well as their active-site mutants sequences into pCDFDuet-1 vector were the following:

DsbCUP—DsbC forward primer introducing the NdeI restriction site:

(SEQ ID NO: 34)
5'GTATTCATATGGATGACGCGGCAATTCAACAAACGTTA3'

DsbCDN—DsbC reverse primer introducing the XhoI restriction site:

(SEQ ID NO: 35)
5'GTTCCCTCGAGTTATTTACCGCTGGTCATTTTTTGGTG3'

DsbDUP—DsbD forward primer introducing the NcoI restriction site:

(SEQ ID NO: 36)
5'GTTATTCGCCATGGGATTATTCGACGCGCCGGGACGTTCA3'

DsbDDN—DsbD reverse primer introducing the EcoRI restriction site:

(SEQ ID NO: 37)
5'GTCTACGAATTCGCTTAAGGCTGTGGCGCTGCGTTGTTGGC3'

The overlap extension oligonucleotide primers that were used to generate the DsbC active site mutants were the following:

DsbCTFfor—active site mutated DsbC (CTFC) overlap extension forward primer:

(SEQ ID NO: 38)
5'TTTACTGATATTACCTGTACCTTCTGCCACAAACTGCATGAG3'

DsbCGFfor—active site mutated DsbC (CGFC) overlap extension forward primer:

(SEQ ID NO: 39)
5'TTTACTGATATTACCTGTGGTTTCTGCCACAAACTGCATGAG3'

DsbCOEback—active site mutated DsbC overlap extension backward primer:

5'ACAGGTAATATCAGTAAACAC3'    (SEQ ID NO: 40)

The pET32a and pCDFDuet-1 external and internal oligonucleotide primers that were employed for sequencing were the following:

DuetCDFUP1:
5'GGATCTCGACGCTCTCCCTTA3'    (SEQ ID NO: 41)

DuetCDFUP2:
5'TTGTACACGGCCGCATAATCG3'    (SEQ ID NO: 42)

```
DuetCDFDN1:
5'CGATTATGCGGCCGTGTACAA3'            (SEQ ID NO: 43)

PETUP1:
5'GGAATTGTGAGCGGATAACAATTC3'         (SEQ ID NO: 44)

PETUP2:
5'CGCGGTTCTGGTATGAAAGAAACC3'         (SEQ ID NO: 45)

PETDN1:
5'GTTATGCTAGTTATTGCTCAGCGG3'         (SEQ ID NO: 46)
```

The bacterial thiol-disulfide interchange protein DsbD α-domain and disulfide isomerase DsbC nucleotide sequences were directly amplified by PCR from E. coli K-12 MG1655 strain genomic DNA prepared and purified in the Francis S. Markland laboratory at the University of Southern California, using the afore-mentioned oligonucleotide primers. The CN sequences were amplified by PCR from plasmids and/or mutated first to replace all native codons that were rarely used in bacteria or those for which Rosetta-gami B did not provide support. The CN nucleotide sequence encompassing the proprotein, metalloproteinase and disintegrin domain was mutated by utilizing the site-directed mutagenesis technique, employing the overlap extension oligonucleotide primers in several PCR steps.

Following PCR amplification of the wild-type full-length CN nucleotide sequence and replacement of optimized codons was completed, and all foldases sequences amplified (with or without active site mutations), these sequences were cloned into pET32a and pCDFDuet-1 vectors in a stepwise manner. The full-length CN nucleotide sequence with replaced codons further served as templates to build the disintegrin constructs including the echistatin C-terminal graft. The wild-type TrxA and the disintegrin nucleotide sequences with or without the echistatin C-terminal graft were directly inserted into the pET32a vector using the BglII/NcoI restriction sites. To build the TrxA-disintegrin constructs with TrxA active site mutants, the TrxA mutants were first separately amplified using the overlap extension primers and then inserted in the pET32a vector to replacing the wild type TrxA sequence using the XbaI/BglII set of restriction enzymes. The pET32a vector including the wild type TrxA nucleotide sequence was used as a template for all the PCR amplification steps necessary to generate TrxA active site mutants. In a further step, after the active site TrxA mutants were inserted into the vector, the disintegrin nucleotide sequences were also inserted in pET32a, by employing the NcoI/EcoRI set of restriction enzymes.

The following active site Trx A mutants were used in the expression system described herein: glutaredoxin-like TrxA (thioredoxin A with a bacterial glutaredoxin A active site) and PDI-like TrxA (thioredoxin A with a eukaryotic protein disulfide isomerase active site).

The active site mutated sequences of ΔssDsbC were directly amplified by PCR from *E. coli* K-12 MG1655 strain genomic DNA using the overlap extension primers. The following active-site mutants were used in the expression system described herein: ΔssDsbC (CGFC (SEQ ID NO: 52)), and ΔssDsbC (CTFC (SEQ ID NO: 53)). The wild-type nucleotide sequences of ΔssDsbD α-domain and ΔssDsbC or the active site mutated sequences of ΔssDsbC were cloned into separate multiple cloning sites of pCDFDuet-1 vector using two sets of restriction enzymes: NcoI/EcoRI and NdeI/XhoI respectively. The pETDuet-1 and pCDFDuet-1 vector constructs were used to co-transform electrocompetent DH5α cells that are further amplified in culture. All constructs were then validated by sequencing and the recombinant plasmids further used to co-transform the Rosetta-gami B expression host.

All growing steps were the same as those previously described for the Origami system, except for the antibody usage. The Rosetta-gami B co-transformants were grown in five antibiotics: carbenicillin (100 μg/mL), spectinomycin (50 μg/mL), tetracycline (12.5 μg/mL), kanamycin (15 μg/mL) and chloramphenicol (34 μg/mL). All processing and purification step of various recombinant proteins were identical to those previously described for the Origami system.

The production level and the biological activity of recombinant disintegrin variants with different co-overexpressed foldases are initially determined after employing the following expression combinations:

1. TrxA-disintegrin+ΔssDsbC+ΔssDsbDα
2. TrxA (CPYC (SEQ ID NO: 49))-disintegrin+ΔssDsbC+ΔssDsbDα
3. TrxA (CGHC (SEQ ID NO: 50))-disintegrin+ΔssDsbC+ΔssDsbDα

By comparing the structures and yields of different TrxA-disintegrin fusion proteins, the version that generates the properly folded dimer at the best level of expression is chosen. To further improve the expression level of correctly folded proteins, the best oxidase version, referred to as "best oxidase-disintegrin," is further tested in combination with two mutated variants of DsbC.

1. Best oxidase-disintegrin+ΔssDsbC (CGFC (SEQ ID NO: 52)+ΔssDsbDα
2. Best oxidase-disintegrin+ΔssDsbC (CTFC (SEQ ID NO: 53)+ΔssDsbDα

For production of recombinant disintegrins the same steps described in Example 1 were employed. However, the expressed recombinant variants including the pro-protein, metalloproteinase and disintegrin domains may undergo a post-translational autocatalytical proteolysis freeing the C-terminal recombinant disintegrin domains with or without echistatin C-terminal graft, disintegrin domains that can be further purified directly from the total soluble protein fraction retrieved form bacteria by reverse-phase HPLC. This desirable event would obviate the need for Ni-column affinity chromatography purification and TEV-protease proteolysis or formic acid hydrolysis intermediary steps employed in recombinant disintegrin production.

Example 5

Optimizing Expression

The system can be optimized to achieve better yields by changing several parameters such as the use of: increased concentrations of carbenicillin (a more stable form of penicillin) that is more resistant to β-lactamase degradation for all growing steps; an optimal IPTG concentration (a feature that can be easily achieved in a Tuner derivative host); and, finally, an optimal induction temperature for generating the best yields. The simplest way to achieve a more homogenous culture and prevent the plasmid loss is to use the more stable antibiotic carbenicillin rather than ampicillin. For tighter regulation of basal expression, a phenomenon that also leads to plasmid instability, the culture medium may be supplemented with 1% glucose to repress induction of the lac promoter by lactose, which is present in most rich media (such as LB). Moreover, addition of small quantities of ethanol, of polyols and sucrose, or low molecular weight thiols can be used to significantly boost the expression of soluble proteins in *E. coli* (e.g., from several milligrams of recombinant protein to tens or even hundreds of milligrams). Also, codon optimization can be used as already discussed. In an effort to optimize the codon usage, the Rosetta-gami B(DE3)pLysS expression host, a strain supplemented with rare tRNAs, may be preferentially employed instead of Origami B(DE3) pLysS.

Example 6

Expression System Combinations

The following elements may be used in obtaining recombinant disintegrin expression. "TP" refers to eukaryotic protein.
1. TrxA-TP or TrxA (CPYC (SEQ ID NO: 49))-TP or TrxA (CGHC (SEQ ID NO: 50) -TP
2. Integrin binding (e.g. HKGPAT (SEQ ID NO: 47)) C-terminal sequence for TP
3. "Tag" sequence for item no. 1.
4. Cleavage site sequence for item no. 1.
5. ΔssDsbC
6. ΔssDsbDα
7. trxB mutant
8. gor mutant
9. ompT mutant
10. lon mutant The methods may include any combination of 1-10 above for expressing TP. In another approach, any of the following elements may be combined for expressing a eukaryotic protein that is not fused to thioredoxin.
1. Eukaryotic protein unfused to thioredoxin
2. Integrin binding (e.g. HKGPAT (SEG ID NO: 47)) C-terminal sequence for TP
3. Tag sequence for item no. 1.
4. Cleavage site sequence for item no. 1.
5. ΔssDsbC
6. ΔssDsbDα
7. trxB mutant
8. gor mutant
9. ompT mutant
10. lon mutant Example 7

Antitumor Activity of CN and Docetaxel

100 μl of PC-3 cell suspension ($1\times10^6$ cells) (ATCC.org, Manassas, Va.) was mixed with an equal volume, 100 μl of Matrigel basement membrane matrix (BD Biosciences, Bedford, Mass.) and injected subcutaneously into the flank region of athymic male nude mice (Balb/c/nu/nu mice) (Charles River Laboratory, Wilmington, Mass.). Four weeks after inoculation, 32 mice with PC-3 tumors were randomized into four groups with 8 mice in each group. The control group was treated with PBS and released from Alzet osmotic mini-pumps for four weeks. The second group was treated with docetaxel injections intraperitoneally at a dose of 6 mg/kg twice a week for two weeks and then switched to 4 mg/kg twice a week for two weeks. The third group was treated with contortrostatin (CN) at a dose of 60 μg/day which was continually released from subcutaneously implanted Alzet osmotic mini-pumps for four weeks. The fourth group was treated with a combination of docetaxel and CN at doses indicated in groups 2 and 3 for four weeks. Tumor volume was measured one a week and are calculated according to the formula: length×width$^2$×0.52.

During the experiment, there were no significant differences in body weights between the groups. Both docetaxel and CN individually significantly suppressed growth of PC-3 tumors. After four weeks, the mean tumor volume was significantly reduced in groups receiving CN or docetaxel with tumor volumes at 195±40 mm$^3$ and 259±38 mm$^3$, respectively as compared with the control group which had a tumor volume of 378±49 mm$^3$ The group receiving a combination of both CN and docetaxel was much more effective that either agent individually. The final tumor volume was significantly ($p<0.01$) reduced to 95±38 mm$^3$. See FIG. 1.

Unless otherwise defined, all technical and scientific terms used herein have the same meaning as commonly understood by one of ordinary skill in the art to which this invention belongs.

The inventions illustratively described herein may suitably be practiced in the absence of any element or elements, limitation or limitations, not specifically disclosed herein. Thus, for example, the terms "comprising," "including," "containing," etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed.

Thus, it should be understood that although the present invention has been specifically disclosed by preferred embodiments and optional features, modification, improvement and variation of the inventions embodied therein herein disclosed may be resorted to by those skilled in the art, and that such modifications, improvements and variations are considered to be within the scope of this invention. The materials, methods, and examples provided here are representative of preferred embodiments, are exemplary, and are not intended as limitations on the scope of the invention.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

In addition, where features or aspects of the invention are described in terms of Markush groups, those skilled in the art will recognize that the invention is also thereby described in terms of any individual member or subgroup of members of the Markush group.

All publications, patent applications, patents, and other references mentioned herein are expressly incorporated by reference in their entirety, including all formulas and figures, to the same extent as if each were incorporated by reference individually. In case of conflict, the present specification, including definitions, will control.

Other embodiments are set forth within the following claims.

That which is claimed is:

1. A method of treating an individual suffering from cancer, said method comprising administering to said individual an effective amount of a disintegrin and at least one microtubule stabilizing agent, wherein said disintegrin is characterized by having an integrin binding loop stabilized by disulfide bonds.

2. The method of claim 1 wherein said cancer is an integrin expressing cancer.

3. The method of claim 2 wherein said integrin is αvβ5.

4. The method of claim 1 wherein said cancer is selected from the group consisting of prostate cancer, breast cancer, lung cancer, colon cancer, ovarian cancer, renal cancer, central nervous system (CNS) cancer, and leukemia.

5. The method of claim 1 wherein said disintegrin is contortrostatin.

6. The method of claim 1 wherein said disintegrin is a contortrostatin monomer.

7. The method of claim 1 wherein said disintegrin is a contortrostatin dimer, a contortrostatin precursor or biologically active variant thereof, containing an amino acid sequence selected from the group consisting of
   (a) amino acid numbers 419 to 483 of SEQ ID NO: 1;
   (b) amino acid numbers 191 to 410 of SEQ ID NO: 1;
   (c) amino acid numbers 1 to 190 of SEQ ID NO: 1; and
   (d) SEQ ID NO: 1.

8. The method of claim 1 wherein said disintegrin is a contortrostatin that comprises a monomer having a molecular mass of about 5 to about 7 kDa.

9. The method of claim 8 wherein said contortrostatin monomer forms a homodimer with another contortrostatin monomer.

10. The method of claim 1 wherein said disintegrin comprises a constrained Arg-Gly-Asp (RGD) sequence of a peptide loop of about 13 amino acid residues flanked by two Cys residues, wherein the peptide loop is an integrin antagonist which has an amino acid sequence comprising amino acid numbers 457 to 469 of SEQ ID NO: 1.

11. The method of claim 1 wherein said disintegrin is vicrostatin.

12. The method of claim 1 wherein said microtubule stabilizing agent is a taxane.

13. The method of claim 12 wherein said taxane is docetaxel.

14. The method of claim 12 wherein said taxane is paclitaxel.

15. The method of claim 12 wherein said taxane has Formula II as follows:

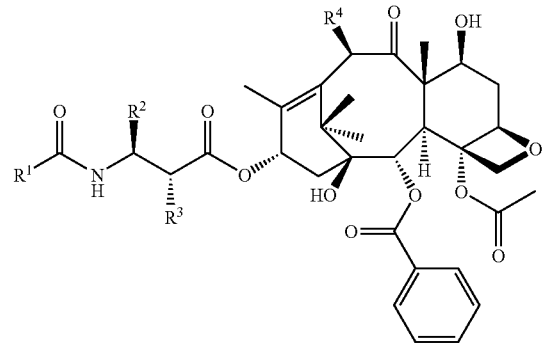

wherein:
$R^1$ and $R^2$ are independently selected from alkyl, alkenyl, cycloalkyl, heterocycloalkyl, aryl, heteroaryl, or oxy, each of which may be optionally substituted;
$R^3$ and $R^4$ are independently selected from alkyl, substituted alkyl, hydroxyl, oxy, C(O)H, or OC(O)$R^5$; and
$R^5$ is alkyl, alkenyl, cycloalkyl, heterocycloalkyl, aryl, or heteroaryl, each of which may be optionally substituted.

16. The method of claim 12 wherein said taxane has Formula III as follows:

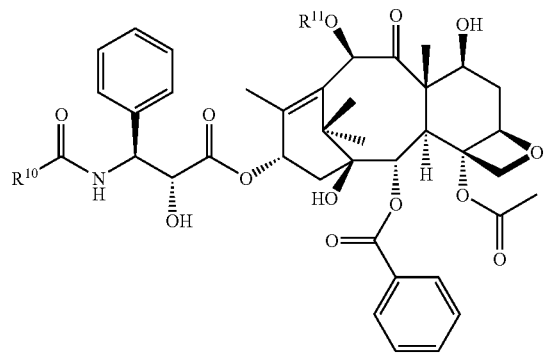

wherein
$R^{10}$ is selected from alkyl, cycloalkyl, aryl or heteroaryl, each of which may be optionally substituted; and
$R^{11}$ is selected from hydrogen, alkyl, —C(O)H, —C(O)CH$_3$, or —C(O)CH$_2$CH$_3$.

17. The method of claim 16 wherein $R^{10}$ is —C(CH$_3$)$_3$ and $R^{11}$ is H.

18. The method of claim 16 wherein $R^{10}$ is phenyl and $R^{11}$ is acetyl.

19. The method of claim 1 wherein said disintegrin is administered before said microtubule stabilizing agent.

20. The method of claim 1 wherein said disintegrin is administered after said microtubule stabilizing agent.

21. The method of claim 1 wherein said disintegrin and microtubule stabilizing agent are co-administered.

22. The method of claim 1 wherein said treatment is repeated.

23. A method of preventing or inhibiting the growth of metastases in an individual suffering from an integrin expressing cancer, said method comprising administering to said individual an effective amount of a disintegrin and at least one microtubule stabilizing agent.

24. The method of claim 23 wherein said cancer is an integrin expressing cancer.

25. The method of claim 24 wherein said integrin is αvβ5.

26. The method of claim 23 wherein said cancer is selected from the group consisting of prostate cancer, breast cancer, lung cancer, colon cancer, ovarian cancer, renal cancer, central nervous system (CNS) cancer, and leukemia.

27. The method of claim 23 wherein said disintegrin is contortrostatin.

28. The method of claim 23 wherein said disintegrin is a contortrostatin monomer.

29. The method of claim 23 wherein said disintegrin is a contortrostatin dimer, a contortrostatin precursor or biologically active variant thereof containing an amino acid sequence selected from the group consisting of:
  (a) amino acid numbers 419 to 483 of SEQ ID NO: 1;
  (b) amino acid numbers 191 to 410 of SEQ ID NO: 1;
  (c) amino acid numbers 1 to 190 of SEQ ID NO: 1; and
  (d) SEQ ID NO: 1.

30. The method of claim 23 wherein said disintegrin is a contortrostatin that comprises a monomer having a molecular mass of about 5 to about 7 kDa.

31. The method of claim 30 wherein said contortrostatin monomer forms a homodimer with another contortrostatin monomer.

32. The method of claim 23 wherein said disintegrin comprises a constrained Arg-Gly-Asp (RGD) sequence of a peptide loop of about 13 amino acid residues flanked by two Cys residues, wherein the peptide loop is an integrin antagonist which has an amino acid sequence comprising amino acid numbers 457 to 469 of SEQ ID NO: 1.

33. The method of claim 23 wherein said disintegrin is vicrostatin.

34. The method of claim 23 wherein said microtubule stabilizing agent is a taxane.

35. The method of claim 34 wherein said taxane is docetaxel.

36. The method of claim 34 wherein said taxane is paclitaxel.

37. The method of claim 34 wherein said taxane has Formula II as follows:

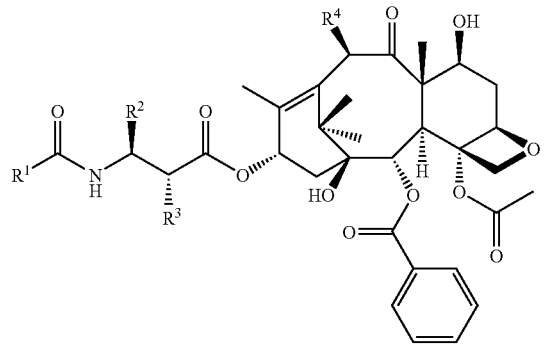

wherein:
  $R^1$ and $R^2$ are independently selected from alkyl, alkenyl, cycloalkyl, heterocycloalkyl, aryl, heteroaryl, or oxy, each of which may be optionally substituted;
  $R^3$ and $R^4$ are independently selected from alkyl, substituted alkyl, hydroxyl, oxy, C(O)H, or OC(O)$R^5$; and
  $R^5$ is alkyl, alkenyl, cycloalkyl, heterocycloalkyl, aryl, or heteroaryl, each of which may be optionally substituted.

38. The method of claim 34 wherein said taxane has Formula III as follows:

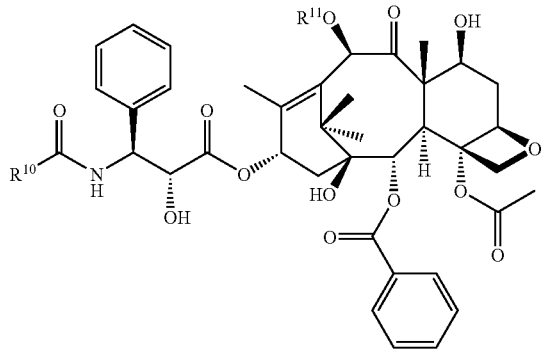

wherein
  $R^{10}$ is selected from alkyl, cycloalkyl, aryl or heteroaryl, each of which may be optionally substituted; and
  $R^{11}$ is selected from hydrogen, alkyl, —C(O)H, —C(O)CH$_3$, or —C(O)CH$_2$CH$_3$.

39. The method of claim 38 wherein $R^{10}$ is —(CH$_3$)$_3$ and $R^{11}$ is H.

40. The method of claim 38 wherein $R^{10}$ is phenyl and $R^{11}$ is acetyl.

41. The method of claim 23 wherein said disintegrin is administered before said microtubule stabilizing agent.

42. The method of claim 23 wherein said disintegrin is administered after said microtubule stabilizing agent.

43. The method of claim 23 wherein said disintegrin and microtubule stabilizing agent are co-administered.

44. The method of claim 23 wherein said treatment is repeated.

45. A method of treating an individual suffering from cancer, said method consisting essentially of administering to said individual an effective amount of a disintegrin and at least one microtubule stabilizing agent, wherein said disintegrin is characterized by having an integrin binding loop stabilized by disulfide bonds.

46. The method of claim 45 wherein said cancer is an integrin expressing cancer.

47. The method of claim 45 wherein said disintegrin is selected from the group consisting of:
(a) vicrostatin;
(b) a contortrostatin monomer;
(c) a contortrostatin dimer; and,
(d) a contortrostatin precursor or biologically active variant thereof, containing an amino acid sequence selected from the group consisting of:
(1) amino acid numbers 419 to 483 of SEQ ID NO: 1;
(2) amino acid numbers 191 to 410 of SEQ ID NO: 1;
(3) amino acid numbers 1 to 190 of SEQ ID NO: 1; and
(4) SEQ ID NO: 1.

48. The method of claim 45 wherein said microtubule stabilizing agent is a taxane.

49. The method of claim 12 wherein said taxane has Formula III as follows:

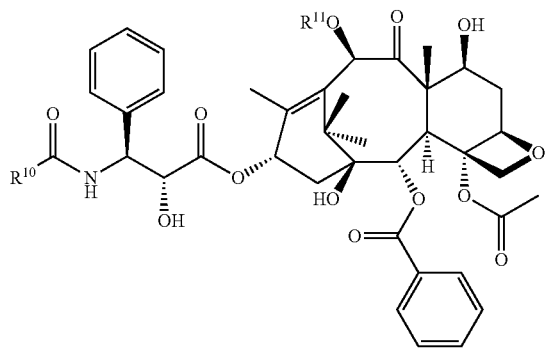

wherein $R^{10}$ is selected from alkyl, cycloalkyl, aryl or heteroaryl, each of which may be optionally substituted; and
$R^{11}$ is selected from hydrogen, alkyl, —C(O)H, —C(O)CH$_3$, or —C(O)CH$_2$CH$_3$.

50. The method of claim 49 wherein $R^{10}$ is —C(CH$_3$)$_3$ and $R^{11}$ is H.

51. The method of claim 49 wherein $R^{10}$ is phenyl and $R^{11}$ is acetyl.

52. A method of preventing or inhibiting the growth of metastases in an individual suffering from an integrin expressing cancer, said method consisting essentially of administering to said individual an effective amount of a disintegrin and at least one microtubule stabilizing agent.

53. The method of claim 52 wherein said taxane has Formula II as follows:

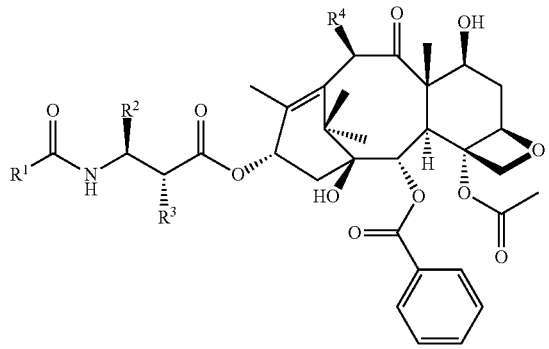

wherein:
$R^1$ and $R^2$ are independently selected from alkyl, alkenyl, cycloalkyl, heterocycloalkyl, aryl, heteroaryl, or oxy, each of which may be optionally substituted;
$R^3$ and $R^4$ are independently selected from alkyl, substituted alkyl, hydroxyl, oxy, C(O)H, or OC(O)R$^5$; and
$R^5$ is alkyl, alkenyl, cycloalkyl, heterocycloalkyl, aryl, or heteroaryl, each of which may be optionally substituted.

54. The method of claim 52 wherein said disintegrin is selected from the group consisting of:
(a) vicrostatin;
(b) a contortrostatin monomer;
(c) a contortrostatin dimer; and
(d) a contortrostatin precursor or biologically active variant thereof, containing an amino acid sequence selected from the group consisting of
(1) amino acid numbers 419 to 483 of SEQ ID NO: 1;
(2) amino acid numbers 191 to 410 of SEQ ID NO: 1;
(3) amino acid numbers 1 to 190 of SEQ ID NO: 1; and
(4) SEQ ID NO: 1.

55. The method of claim 52 wherein said microtubule stabilizing agent is a taxane.

56. The method of claim 55 wherein said taxane has Formula II as follows:

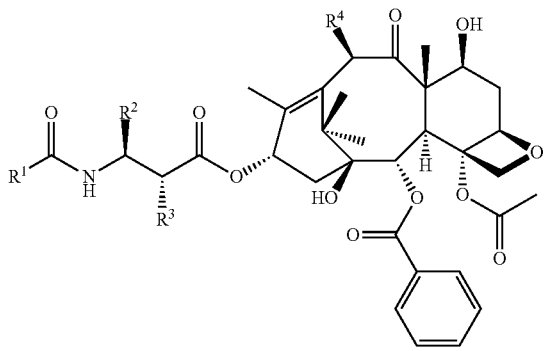

wherein:
$R^1$ and $R^2$ are independently selected from alkyl, alkenyl, cycloalkyl, heterocycloalkyl, aryl, heteroaryl, or oxy, each of which may be optionally substituted;
$R^3$ and $R^4$ are independently selected from alkyl, substituted alkyl, hydroxyl, oxy, C(O)H, or OC(O)R$^5$; and
$R^5$ is alkyl, alkenyl, cycloalkyl, heterocycloalkyl, aryl, or heteroaryl, each of which may be optionally substituted.

57. The method of claim 55 wherein said taxane has Formula III as follows:

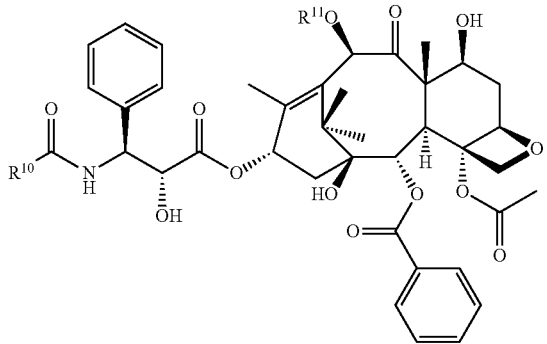

wherein
$R^{10}$ is selected from alkyl, cycloalkyl, aryl or heteroaryl, each of which may be optionally substituted; and
$R^{11}$ is selected from hydrogen, alkyl, —C(O)H, —C(O)CH$_3$, or —C(O)CH$_2$CH$_3$.

58. The method of claim 57 wherein $R^{10}$ is —C(CH$_3$)$_3$ and $R^{11}$ is H.

59. The method of claim 57 wherein $R^{10}$ is phenyl and $R^{11}$ is acetyl.

* * * * *

SEQUENCE LISTING

<160> NUMBER OF SEQ ID NOS: 54

<210> SEQ ID NO 1
<211> LENGTH: 483
<212> TYPE: PRT
<213> ORGANISM: Agkistrodon contortrix contortrix

<400> SEQUENCE: 1

```
Met Ile Gln Val Leu Leu Val Thr Leu Cys Leu Ala Ala Phe Pro Tyr
1               5                   10                  15

Gln Gly Ser Ser Ile Ile Leu Glu Ser Gly Asn Val Asn Asp Tyr Glu
            20                  25                  30

Val Leu Tyr Pro Gln Lys Val Thr Ala Leu Pro Lys Gly Ala Val Gln
        35                  40                  45

Pro Lys Tyr Glu Asp Thr Met Gln Tyr Glu Phe Lys Val Asn Gly Glu
    50                  55                  60

Pro Val Val Leu His Leu Glu Lys Asn Lys Gly Leu Phe Ser Lys Asp
65                  70                  75                  80

Tyr Ser Glu Thr His Tyr Ser Ser Asp Gly Arg Lys Ile Thr Thr Asn
                85                  90                  95

Pro Pro Val Glu Asp His Cys Tyr Tyr His Gly Arg Ile Gln Asn Asp
            100                 105                 110

Ala Asp Ser Thr Ala Ser Ile Ser Ala Cys Asn Gly Leu Lys Gly His
        115                 120                 125

Phe Lys Leu Gln Gly Glu Thr Tyr Leu Ile Glu Pro Leu Lys Leu Ser
    130                 135                 140

Asp Ser Glu Ala His Ala Val Tyr Lys Tyr Glu Asn Val Glu Lys Glu
145                 150                 155                 160

Asp Glu Ala Pro Lys Met Cys Gly Val Thr Gln Thr Asn Trp Glu Ser
                165                 170                 175

Asp Glu Pro Ile Lys Lys Ala Ser Gln Leu Asn Leu Thr Pro Glu Gln
            180                 185                 190

Gln Gly Phe Pro Gln Arg Tyr Ile Glu Leu Val Val Val Ala Asp His
        195                 200                 205

Arg Met Phe Thr Lys Tyr Asn Gly Asn Leu Asn Thr Ile Arg Ile Trp
    210                 215                 220

Val His Glu Leu Val Asn Thr Met Asn Val Phe Tyr Arg Pro Leu Asn
225                 230                 235                 240

Ile Arg Val Ser Leu Thr Asp Leu Glu Val Trp Ser Asp Gln Asp Leu
                245                 250                 255

Ile Asn Val Gln Pro Ala Ala Ala Asp Thr Leu Glu Ala Phe Gly Asp
            260                 265                 270

Trp Arg Glu Thr Val Leu Leu Asn Arg Ile Ser His Asp Asn Ala Gln
        275                 280                 285

Leu Leu Thr Ala Ile Glu Leu Asp Gly Glu Thr Ile Gly Leu Ala Asn
    290                 295                 300

Arg Gly Thr Met Cys Asp Pro Lys Leu Ser Thr Gly Ile Val Gln Asp
305                 310                 315                 320

His Ser Ala Ile Asn Leu Trp Val Ala Val Thr Met Ala His Glu Met
                325                 330                 335

Gly His Asn Leu Gly Ile Ser His Asp Gly Asn Gln Cys His Cys Asp
            340                 345                 350

Ala Asn Ser Cys Ile Met Ser Glu Glu Leu Arg Glu Gln Leu Ser Phe
        355                 360                 365
```

| Glu | Phe | Ser | Asp | Cys | Ser | Gln | Asn | Gln | Tyr | Gln | Thr | Tyr | Leu | Thr | Asp |
| | 370 | | | | | 375 | | | | | 380 | | | | |

| His | Asn | Pro | Gln | Cys | Met | Leu | Asn | Glu | Pro | Leu | Arg | Thr | Asp | Ile | Val |
| 385 | | | | | 390 | | | | | 395 | | | | | 400 |

| Ser | Thr | Pro | Val | Ser | Gly | Asn | Glu | Leu | Leu | Glu | Thr | Gly | Glu | Glu | Ser |
| | | | | 405 | | | | | 410 | | | | | 415 | |

| Asp | Phe | Asp | Ala | Pro | Ala | Asn | Pro | Cys | Cys | Asp | Ala | Thr | Cys | Lys |
| | | | 420 | | | | | 425 | | | | | 430 | |

| Leu | Thr | Thr | Gly | Ser | Gln | Cys | Ala | Asp | Gly | Leu | Cys | Cys | Asp | Gln | Cys |
| | | | 435 | | | | | 440 | | | | | 445 | | |

| Lys | Phe | Met | Lys | Glu | Gly | Thr | Val | Cys | Arg | Arg | Ala | Arg | Gly | Asp | Asp |
| | 450 | | | | | 455 | | | | | 460 | | | | |

| Leu | Asp | Asp | Tyr | Cys | Asn | Gly | Ile | Ser | Ala | Gly | Cys | Pro | Arg | Asn | Pro |
| 465 | | | | | 470 | | | | | 475 | | | | | 480 |

Phe His Ala

<210> SEQ ID NO 2
<211> LENGTH: 2029
<212> TYPE: DNA
<213> ORGANISM: Agkistrodon contortrix contortrix

<400> SEQUENCE: 2

```
gaattcgggg tcaatagagg aagagctcaa gttggcttga aagcaggaag agattgcctg    60
tcttccagcc aaatccagcc gccaaaatga tccaggttct cttggtgact ctatgcttag   120
cagcttttcc ttatcaaggg agctctataa tcctggaatc tgggaatgtt aatgattatg   180
aagtactgta tccacaaaaa gtcactgcat tgcccaaagg agcagttcag ccaaagtatg   240
aagacaccat gcaatatgaa tttaaagtga atggagagcc agtggtcctt cacctggaaa   300
aaaataaagg actttttttca aaagattaca gcgagactca ttattcctct gatggcagaa   360
aaattacaac aaaccctccg gttgaggatc actgctatta tcatggacgc atccagaatg   420
atgctgactc aactgcaagc atcagtgcat gcaacggttt gaaaggacat ttcaagcttc   480
aaggggagac gtaccttatt gaacccttga gctttccga cagtgaagcc catgcagtct   540
acaaatatga aaacgtagaa aagaagatg aggcccccaa atgtgtgggg gtaacccaga   600
ctaattggga atcagatgag cccatcaaaa aggcctctca gttaaatctt actcctgaac   660
aacaaggatt ccccaaaga tacattgagc ttgttgtagt tgcagatcac agaatgttca   720
cgaaatacaa cggcaattta atactatta gaatatgggt acatgaactt gtcaacacta   780
tgaatgtgtt ttacagacct ttgaatattc gtgtctcact gactgaccta aagtttggt   840
cagaccaaga tttgatcaac gtgcagccag cagcggctga tacttttgaa gcatttggag   900
actggagaga gacagtcttg ctgaatcgca taagtcatga taatgctcag ttactcacgg   960
ccattgagct tgatggagaa actataggat tggctaacag gggcaccatg tgcgacccga  1020
agctttctac aggaattgtt caggatcata gtgcaataaa tctttgggtt gcagttacaa  1080
tgccccatga gatgggtcat aatctgggta ttagtcacga tggaaatcag tgtcattgcg  1140
atgctaactc atgcattatg agtgaagaac taagagaaca actttccttt gagttcagcg  1200
attgtagtca gaatcaatat cagacatatc ttactgatca taaccacaa tgcatgctca  1260
atgaacccct tagaacagat attgtttcaa ctccagtttc tggaaatgaa cttttggaga  1320
cgggagaaga aagtgacttt gacgctcctg caaatccgtg ctgcgatgct gcaacatgta  1380
aactgacaac agggtcacag tgtgcagatg gactgtgttg tgaccagtgc aaatttatga  1440
```

-continued

```
aagaaggaac agtatgccgg agagcaaggg gtgatgacct ggatgattac tgcaatggca   1500
tatctgctgg ctgtcccaga atcccttcc atgcctaacc aacaatggag atggaatggt    1560
ctgcagcaac aggcagtgtg ttgatctgaa tacagcctaa taatcaacct ctggcttctc   1620
tcagatttga tcatggagat ccttcttcca gaaggtttca cttccctcaa atccaaagag   1680
acccatctgc ctgcatccta ctagtaaatc acccttagct tccagatggt atccaaattc   1740
tgtaatattt cttctccata tttaatctat ttaccttttg ctgtaacaaa accttttttcc  1800 tgtcacaaag ctccatgggc atgtacagct tatctgctgt caagaaaaaa aatggccatt   1860
ttaccgtttg ccagttacaa agcacattta atgcaacaag ttcttccttt tgagctgatg   1920
tattcaaagt caatgcttcc tctcccaaaa tttcatgctg gcttcccaag atgtagctgc   1980
ttccgtcaat aaacaaacta ttctcattca aaaaaaaaaa cccgaattc               2029
```

<210> SEQ ID NO 3
<211> LENGTH: 65
<212> TYPE: PRT
<213> ORGANISM: Agkistrodon contortrix contortrix

<400> SEQUENCE: 3

Asp Ala Pro Ala Asn Pro Cys Cys Asp Ala Ala Thr Cys Lys Leu Thr
1               5                   10                  15

Thr Gly Ser Gln Cys Ala Asp Gly Leu Cys Cys Asp Gln Cys Lys Phe
            20                  25                  30

Met Lys Glu Gly Thr Val Cys Arg Arg Ala Arg Gly Asp Asp Leu Asp
        35                  40                  45

Asp Tyr Cys Asn Gly Ile Ser Ala Gly Cys Pro Arg Asn Pro Phe His
    50                  55                  60

Ala
65

<210> SEQ ID NO 4
<211> LENGTH: 109
<212> TYPE: PRT
<213> ORGANISM: Escherichia coli

<400> SEQUENCE: 4

Met Ser Asp Lys Ile Ile His Leu Thr Asp Asp Ser Phe Asp Thr Asp
1               5                   10                  15

Val Leu Lys Ala Asp Gly Ala Ile Leu Val Asp Phe Trp Ala Glu Trp
            20                  25                  30

Cys Gly Pro Cys Lys Met Ile Ala Pro Ile Leu Asp Glu Ile Ala Asp
        35                  40                  45

Glu Tyr Gln Gly Lys Leu Thr Val Ala Lys Leu Asn Ile Asp Gln Asn
    50                  55                  60

Pro Gly Thr Ala Pro Lys Tyr Gly Ile Arg Gly Ile Pro Thr Leu Leu
65                  70                  75                  80

Leu Phe Lys Asn Gly Glu Val Ala Ala Thr Lys Val Gly Ala Leu Ser
                85                  90                  95

Lys Gly Gln Leu Lys Glu Phe Leu Asp Ala Asn Leu Ala
            100                 105

<210> SEQ ID NO 5
<211> LENGTH: 216
<212> TYPE: PRT
<213> ORGANISM: Escherichia coli
<220> FEATURE:
<221> NAME/KEY: MOD_RES
<222> LOCATION: (206)..(206)

<223> OTHER INFORMATION: Any amino acid

<400> SEQUENCE: 5

```
Asp Asp Ala Ala Ile Gln Gln Thr Leu Ala Lys Met Gly Ile Lys Ser
1               5                   10                  15

Ser Asp Ile Gln Pro Ala Pro Val Ala Gly Met Lys Thr Val Leu Thr
            20                  25                  30

Asn Ser Gly Val Leu Tyr Ile Thr Asp Asp Gly Lys His Ile Ile Gln
        35                  40                  45

Gly Pro Met Tyr Asp Val Ser Gly Thr Ala Pro Val Asn Val Thr Asn
    50                  55                  60

Lys Met Leu Leu Lys Gln Leu Asn Ala Leu Glu Lys Glu Met Ile Val
65                  70                  75                  80

Tyr Lys Ala Pro Gln Glu Lys His Val Ile Thr Val Phe Thr Asp Ile
                85                  90                  95

Thr Cys Gly Tyr Cys His Lys Leu His Glu Gln Met Ala Asp Tyr Asn
            100                 105                 110

Ala Leu Gly Ile Thr Val Arg Tyr Leu Ala Phe Pro Arg Gln Gly Leu
        115                 120                 125

Asp Ser Asp Ala Glu Lys Glu Met Lys Ala Ile Trp Cys Ala Lys Asp
    130                 135                 140

Lys Asn Lys Ala Phe Asp Asp Val Met Ala Gly Lys Ser Val Ala Pro
145                 150                 155                 160

Ala Ser Cys Asp Val Asp Ile Ala Asp His Tyr Ala Leu Gly Val Gln
                165                 170                 175

Leu Gly Val Ser Gly Thr Pro Ala Val Val Leu Ser Asn Gly Thr Leu
            180                 185                 190

Val Pro Gly Tyr Gln Pro Lys Glu Met Lys Glu Phe Xaa Asp Glu
        195                 200                 205

His Gln Lys Met Thr Ser Gly Lys
    210                 215
```

<210> SEQ ID NO 6
<211> LENGTH: 132
<212> TYPE: PRT
<213> ORGANISM: Escherichia coli

<400> SEQUENCE: 6

```
Gly Leu Phe Asp Ala Pro Gly Arg Ser Gln Phe Val Pro Ala Asp Gln
1               5                   10                  15

Ala Phe Ala Phe Asp Phe Gln Gln Asn Gln His Asp Leu Asn Leu Thr
            20                  25                  30

Trp Gln Ile Lys Asp Gly Tyr Tyr Leu Tyr Arg Lys Gln Ile Arg Ile
        35                  40                  45

Thr Pro Glu His Ala Lys Ile Ala Asp Val Gln Leu Pro Gln Gly Val
    50                  55                  60

Trp His Glu Asp Glu Phe Tyr Gly Lys Ser Glu Ile Tyr Arg Asp Arg
65                  70                  75                  80

Leu Thr Leu Pro Val Thr Ile Asn Gln Ala Ser Ala Gly Ala Thr Leu
                85                  90                  95

Thr Val Thr Tyr Gln Gly Cys Ala Asp Ala Gly Phe Cys Tyr Pro Pro
            100                 105                 110

Glu Thr Lys Thr Val Pro Leu Ser Glu Val Val Ala Asn Asn Glu Ala
        115                 120                 125

Ser Gln Pro Val
    130
```

```
<210> SEQ ID NO 7
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(7)
<223> OTHER INFORMATION: Gly or Ser

<400> SEQUENCE: 7

Glu Asn Leu Tyr Phe Gln Xaa
1               5

<210> SEQ ID NO 8
<211> LENGTH: 69
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Gly Asp Ala Pro Ala Asn Pro Cys Cys Asp Ala Ala Thr Cys Lys Leu
1               5                   10                  15

Thr Thr Gly Ser Gln Cys Ala Asp Gly Leu Cys Cys Asp Gln Cys Lys
            20                  25                  30

Phe Met Lys Glu Gly Thr Val Cys Arg Arg Ala Arg Gly Asp Asp Leu
        35                  40                  45

Asp Asp Tyr Cys Asn Gly Ile Ser Ala Gly Cys Pro Arg Asn Pro His
    50                  55                  60

Lys Gly Pro Ala Thr
65

<210> SEQ ID NO 9
<211> LENGTH: 66
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
gttccagatc tcgagaatct ttacttccaa ggagacgctc ctgcaaatcc gtgctgcgat    60
gctgca                                                              66

<210> SEQ ID NO 10
<211> LENGTH: 51
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
gttattcgcc atggcttagg catggaaggg atttctggga cagccagcag a             51

<210> SEQ ID NO 11
<211> LENGTH: 66
<212> TYPE: DNA
<213> ORGANISM: Artificial Sequence
<220> FEATURE:
<223> OTHER INFORMATION: Description of Artificial Sequence: Synthetic
``` primer

<400> SEQUENCE: 11
gttattcgcc atggcttaag tagctggacc cttgtgggga tttctgggac agccagcaga     60
tatgcc                                                                66

<210> SEQ ID NO 12
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
accgtatgcc gtagagcaag gggtgatgac ctggatgatt ac                        42

<210> SEQ ID NO 13
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
tgctctacgg catacggttc cttctttcat aaatttgcac tg                        42

<210> SEQ ID NO 14
<211> LENGTH: 48
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
tgcgatgctg caacctgtaa actgaccacc gggtcacagt gtgcagat                  48

<210> SEQ ID NO 15
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
cagtttacag gttgcagcat cgcagcacgg atttgc                               36

<210> SEQ ID NO 16
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
tctgatggca gaaaaattac caccaaccct ccggttgag                            39

<210> SEQ ID NO 17
<211> LENGTH: 27
<212> TYPE: DNA
<213> ORGANISM: Artificial Sequence
<220> FEATURE:
<223> OTHER INFORMATION: Description of Artificial Sequence: Synthetic primer

<400> SEQUENCE: 17
aatttttctg ccatcagagg aataatg         27

<210> SEQ ID NO 18
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
catagtgcaa taaatctttg ggttgcagtt actatggccc atgag         45

<210> SEQ ID NO 19
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
atttattgca ctatgatcct gaacaattcc ggtagaaagc ttcgg         45

<210> SEQ ID NO 20
<211> LENGTH: 67
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
gttccccatg gatgagaatc tttacttcca aggagacgct cctgcaaatc cgtgctgcga    60
tgctgca            67

<210> SEQ ID NO 21
<211> LENGTH: 67
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
gttccccatg gatgagaatc tttacttcca aggaatgatc caggttctct tggtgactct    60
atgctta            67

<210> SEQ ID NO 22
<211> LENGTH: 50
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
gttattcgga attcttaggc atggaaggga tttctgggac agccagcaga         50

<210> SEQ ID NO 23
<211> LENGTH: 65
<212> TYPE: DNA
<213> ORGANISM: Artificial Sequence

```
<220> FEATURE:
<223> OTHER INFORMATION: Description of Artificial Sequence: Synthetic
      primer

<400> SEQUENCE: 23
gttattcgga attcttaagt agctggaccc ttgtggggat ttctgggaca gccagcagat    60
atgcc                                                               65

<210> SEQ ID NO 24
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
gttattcgga attcatatta cagaatttgg ataccatctg gaagcta                 47

<210> SEQ ID NO 25
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
gttattcgga attcgaatga gaatagtttg tttattgacg gaagcag                 47

<210> SEQ ID NO 26
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
cccctctaga aataattttg tttaact                                       27

<210> SEQ ID NO 27
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
tacccagatc tgggctgtcc atgtgct                                       27

<210> SEQ ID NO 28
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
ttctgggcag agtggtgccc gtattgcaaa atgatcgccc cg                      42

<210> SEQ ID NO 29
<211> LENGTH: 21
<212> TYPE: DNA
<213> ORGANISM: Artificial Sequence
```

<220> FEATURE:
<223> OTHER INFORMATION: Description of Artificial Sequence: Synthetic primer

<400> SEQUENCE: 29
gcaccactct gcccagaaat c                                              21

<210> SEQ ID NO 30
<211> LENGTH: 42
<212> TYPE: DNA
<213> ORGANISM: Artificial Sequence
<220> FEATURE:
<223> OTHER INFORMATION: Description of Artificial Sequence: Synthetic primer

<400> SEQUENCE: 30
ttctgggcag agtggtgcgg tcattgcaaa atgatcgccc cg                       42

<210> SEQ ID NO 31
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 31
gcaccactct gcccagaaat c                                              21

<210> SEQ ID NO 32
<211> LENGTH: 46
<212> TYPE: DNA
<213> ORGANISM: Artificial Sequence
<220> FEATURE:
<223> OTHER INFORMATION: Description of Artificial Sequence: Synthetic primer

<400> SEQUENCE: 32
gttccccatg gatgaccctg caaatccgtg ctgcgatgct gcaaca                   46

<210> SEQ ID NO 33
<211> LENGTH: 52
<212> TYPE: DNA
<213> ORGANISM: Artificial Sequence
<220> FEATURE:
<223> OTHER INFORMATION: Description of Artificial Sequence: Synthetic primer

<400> SEQUENCE: 33
gttccccatg gatgaccta tgatccaggt tctcttggtg actctatgct ta             52

<210> SEQ ID NO 34
<211> LENGTH: 38
<212> TYPE: DNA
<213> ORGANISM: Artificial Sequence
<220> FEATURE:
<223> OTHER INFORMATION: Description of Artificial Sequence: Synthetic primer

<400> SEQUENCE: 34
gtattcatat ggatgacgcg gcaattcaac aaacgtta                            38

<210> SEQ ID NO 35
<211> LENGTH: 38
<212> TYPE: DNA
<213> ORGANISM: Artificial Sequence
<220> FEATURE:
<223> OTHER INFORMATION: Description of Artificial Sequence: Synthetic -continued primer

<400> SEQUENCE: 35
gttccctcga gttatttacc gctggtcatt ttttggtg                                38

<210> SEQ ID NO 36
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
gttattcgcc atgggattat tcgacgcgcc gggacgttca                              40

<210> SEQ ID NO 37
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37
gtctacgaat tcgcttaagg ctgtggcgct gcgttgttgg c                            41

<210> SEQ ID NO 38
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38
tttactgata ttacctgtac cttctgccac aaactgcatg ag                           42

<210> SEQ ID NO 39
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 39
tttactgata ttacctgtgg tttctgccac aaactgcatg ag                           42

<210> SEQ ID NO 40
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 40
acaggtaata tcagtaaaca c                                                  21

<210> SEQ ID NO 41
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 41
ggatctcgac gctctccctt a                                              21

<210> SEQ ID NO 42
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 42
ttgtacacgg ccgcataatc g                                              21

<210> SEQ ID NO 43
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 43
cgattatgcg gccgtgtaca a                                              21

<210> SEQ ID NO 44
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 44
ggaattgtga gcggataaca attc                                           24

<210> SEQ ID NO 45
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 45
cgcggttctg gtatgaaaga aacc                                           24

<210> SEQ ID NO 46
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 46
gttatgctag ttattgctca gcgg                                           24

<210> SEQ ID NO 47
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47
```

```
His Lys Gly Pro Ala Thr
1               5

<210> SEQ ID NO 48
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Cys Gly Pro Cys
1

<210> SEQ ID NO 49
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Cys Pro Tyr Cys
1

<210> SEQ ID NO 50
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Cys Gly His Cys
1

<210> SEQ ID NO 51
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Cys Gly Tyr Cys
1

<210> SEQ ID NO 52
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Cys Gly Phe Cys
1

<210> SEQ ID NO 53
<211> LENGTH: 4
<212> TYPE: PRT
<213> ORGANISM: Artificial Sequence
<220> FEATURE:
<223> OTHER INFORMATION: Description of Artificial Sequence: Synthetic
```

```
                             -continued
    peptide

<400> SEQUENCE: 53

Cys Thr Phe Cys
1

<210> SEQ ID NO 54
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Glu Asn Leu Tyr Phe Gln Gly
1               5
```